United States Patent
Parthasarathy et al.

(10) Patent No.: US 7,192,560 B2
(45) Date of Patent: Mar. 20, 2007

(54) METHODS AND DEVICES FOR REMOVAL OF ORGANIC MOLECULES FROM BIOLOGICAL MIXTURES USING ANION EXCHANGE

(75) Inventors: Ranjani V. Parthasarathy, Woodbury, MN (US); Raj Rajagopal, Woodbury, MN (US); Erin E. Olson, St. Paul, MN (US); Frank J. Beissel, IV, Lakeville, MN (US); William Bedingham, Woodbury, MN (US); Barry W. Robole, Woodville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 554 days.

(21) Appl. No.: 10/027,222

(22) Filed: Dec. 20, 2001

(65) Prior Publication Data

US 2003/0138779 A1 Jul. 24, 2003

(51) Int. Cl.
*B01L 11/00* (2006.01)

(52) U.S. Cl. .............. 422/101; 422/100; 422/102; 436/161; 436/174; 436/175; 436/177; 436/178

(58) Field of Classification Search .......... 436/161, 436/174, 175, 177, 178; 422/68.1, 99, 100, 422/102, 101, 103; 435/7.1, 72, 283.1, 287.1, 435/287.3, 287.8, 287.9, 288.2, 288.4, 288.5
See application file for complete search history.

(56) References Cited

U.S. PATENT DOCUMENTS

| | | | |
|---|---|---|---|
| 3,157,635 A | 11/1964 | Tamaka et al. | .......... 260/211.5 |
| 4,399,009 A | 8/1983 | Chisholm | |

(Continued)

FOREIGN PATENT DOCUMENTS

| | | |
|---|---|---|
| DE | 197 31 670 A1 | 1/1999 |
| WO | WO 92/16659 | 10/1992 |

(Continued)

OTHER PUBLICATIONS

"ABI Prism® BigDye™ Terminators v3.0 Cycle Sequencing Kit," product information [online]. Applied Biosystems, 2000, 2001 [retrieved Dec. 3, 2001]. Retrieved from the Internet: <URL:http://www.appliedbiosystems.com/products/productdetail.cfm?id=81>, 1 page.

American Society of Testing Materials, "ASTM D 570–98, Standard Test Method for Water Absorption of Plastics," *Annual Book of ASTM Standards*, 3 pages (1998).

"AutoSeq96 Dye Terminator Clean–up Kit/Adapter Plate for AutoSeq96," product catologue [online]. Amersham Biosciences, 2001 [retrieved Dec. 3, 2001]. Retrieved from the Internet: <URL:http://www.apbiotech.com/stiboasp/showmodule.asp?nModuleid=164360>, 2 pages.

"BLAST," National Institutes of Health [online] United States, [retrieved Apr. 19, 2002]. Retrieved from the Internet:<URL:http://www.ncbi.nlm.nih.gov/BLAST/>, 2 pages.

Boom et al., "Rapid and Simple Method for Purification of Nucleic Acids," *Journal of Clinical Microbiology*, Mar. 1990; vol. 28, No. 3; pp. 495–503.

"Porex Corporate Profile," [online]. Porex Corporation, 2001 [retrieved Dec. 5, 2001]. Retrieved from the Internet: <URL:http://www.porex.com/english/corporate/index.asp>, 3 pages.

(Continued)

*Primary Examiner*—Jill Warden
*Assistant Examiner*—Dwayne K. Handy
(74) *Attorney, Agent, or Firm*—Nancy M. Lambert

(57) ABSTRACT

Methods and devices for removing small negatively charged molecules from a biological sample mixture that uses an anion exchange material.

47 Claims, 2 Drawing Sheets

U.S. PATENT DOCUMENTS

| | | | |
|---|---|---|---|
| 4,780,367 A | | 10/1988 | Lau et al. |
| 4,923,978 A | | 5/1990 | McCormick |
| 5,183,705 A | | 2/1993 | Birkholz et al. |
| 5,187,066 A | | 2/1993 | Becker et al. |
| 5,294,668 A | | 3/1994 | Babu |
| 5,334,316 A | | 8/1994 | Bruening et al. |
| 5,380,901 A | | 1/1995 | Antonucci et al. |
| 5,620,663 A | | 4/1997 | Aysta et al. |
| 5,633,290 A | | 5/1997 | Frechet et al. |
| 5,741,828 A | | 4/1998 | Stoy et al. |
| 5,801,237 A | | 9/1998 | Johansson |
| 5,834,583 A | | 11/1998 | Hancock et al. |
| 5,997,818 A | | 12/1999 | Hacker et al. |
| 6,007,690 A | | 12/1999 | Nelson et al. |
| 6,048,550 A | | 4/2000 | Chan et al. |
| 6,063,838 A | | 5/2000 | Patnode et al. |
| 6,071,406 A | | 6/2000 | Tsou |
| 6,074,827 A | | 6/2000 | Nelson et al. |
| 6,093,558 A | | 7/2000 | Seed et al. |
| 6,103,199 A | | 8/2000 | Bjornson et al. |
| 6,143,247 A | * | 11/2000 | Sheppard et al. ............. 422/63 |
| 6,197,595 B1 | * | 3/2001 | Anderson et al. ........... 436/180 |
| 6,265,168 B1 | * | 7/2001 | Gjerde et al. .................. 435/6 |
| 6,277,488 B1 | | 8/2001 | Kobe et al. |
| 6,284,113 B1 | | 9/2001 | Bjornson et al. |
| 6,306,273 B1 | | 10/2001 | Wainright et al. |
| 6,319,469 B1 | * | 11/2001 | Mian et al. ................... 422/64 |
| 6,344,326 B1 | * | 2/2002 | Nelson et al. ................. 435/6 |
| 6,450,047 B2 | * | 9/2002 | Swedberg et al. ............ 73/863 |
| 6,451,260 B1 | * | 9/2002 | Dusterhoft et al. ........ 422/68.1 |
| 6,504,021 B2 | | 1/2003 | Kristyanne et al. |
| 6,632,399 B1 | | 10/2003 | Kellogg et al. |
| 2001/0045000 A1 | * | 11/2001 | Gundel et al. ................ 29/458 |
| 2002/0046966 A1 | * | 4/2002 | Muscate-Magnussen . 210/198.2 |
| 2002/0182114 A1 | * | 12/2002 | Ingenhoven et al. .......... 422/99 |
| 2003/0013203 A1 | * | 1/2003 | Jedrzejewski et al. ...... 436/102 |
| 2003/0053934 A1 | * | 3/2003 | Andersson et al. ........... 422/72 |
| 2003/0062310 A1 | * | 4/2003 | Zare et al. ................... 210/656 |
| 2003/0228706 A1 | | 12/2003 | Ramstad et al. |
| 2004/0016702 A1 | | 1/2004 | Hennessy et al. |
| 2004/0018116 A1 | | 1/2004 | Desmond et al. |
| 2004/0018559 A1 | | 1/2004 | Lau et al. |

FOREIGN PATENT DOCUMENTS

| | | |
|---|---|---|
| WO | WO 95/24505 A1 | 9/1995 |
| WO | WO 97/27325 A2 | 7/1997 |
| WO | WO 97/27325 A3 | 7/1997 |
| WO | WO 98/04909 A1 | 2/1998 |
| WO | WO 99/15876 A1 | 4/1999 |
| WO | WO 99/15888 A1 | 4/1999 |
| WO | WO 99/39120 A1 | 8/1999 |
| WO | WO 99/40174 A1 | 8/1999 |
| WO | WO 99/46591 A3 | 9/1999 |
| WO | WO 99/46591 A2 | 9/1999 |
| WO | WO 99/58664 A1 | 11/1999 |
| WO | WO 00/45180 A1 | 8/2000 |
| WO | WO 00/62051 A3 | 10/2000 |
| WO | WO 00/62051 A2 | 10/2000 |
| WO | WO 00/68336 A1 | 11/2000 |
| WO | WO 01/03149 A1 | 1/2001 |
| WO | WO 01/12327 A1 | 2/2001 |
| WO | WO 01/21632 A1 | 3/2001 |
| WO | WO 01/25490 A1 | 4/2001 |
| WO | WO 01/25491 A1 | 4/2001 |
| WO | WO 01/38516 A1 | 5/2001 |
| WO | WO 01/38865 A1 | 5/2001 |
| WO | WO 01/68240 A2 | 9/2001 |
| WO | WO 01/68240 A3 | 9/2001 |
| WO | WO 01/68913 A2 | 9/2001 |
| WO | WO 01/71732 A2 | 9/2001 |
| WO | WO 01/71732 A3 | 9/2001 |
| WO | WO 04/009851 A2 | 1/2004 |
| WO | WO 04/010760 A2 | 2/2004 |
| WO | WO 04/011141 A1 | 2/2004 |
| WO | WO 04/011142 A1 | 2/2004 |
| WO | WO 04/011592 A2 | 2/2004 |
| WO | WO 04/011681 A1 | 2/2004 |

OTHER PUBLICATIONS

"Porex Products Group," profile [online]. Porex Corporation, 2001 [retrieved Dec. 5, 2001]. Retrieved from the Internet: <URL:http://www.porex.com/english/porous/index.asp>, 2 pages.

"Purification so fast it'll make your head spin: RapTract Dye Terminator Removal Kit," Prolinx Product Information, Bothell, WA, 2000, 6 pages.

Takeuchi et al., "Ion Chromatography Using Anion Exchangers Modified with Anionic Polysaccharides," LCGC Magazine [online]. LCGC North America, 2001 [retrieved Oct. 02, 2001]. Retrieved from the Internet: <URL:http://www.lcgcmag.com/articles/0004_articles/0004_Takeuchi/0004_Takeuchi.asp>, 12 pages.

"3M Empore Products 96–Well Plates," product listing [online]. 3M Corporation, 1999 [retrieved Dec. 5, 2001]. Retrieved from the Internet: <URL:http://www.mmm.com/empore/formats/Plates/sorbavlb/index.htm>, 2 pages.

"3M Empore Products Empore 96–Well Plates" SPE Extraction Disk Plates & Filter Plates, 3M Extraction Disk Plates for SPE, product listing [online]. 3M Corporation, 1999 [retrieved Dec. 5, 2001]. Retrieved from the Internet: 21 URL:http://www.mmm.com/empore/formats/Plates/index.htm>, 2 pages.

Tong, et al., "Solid–Phase Method for the Purification of DNA Sequencing Reactions," *Analytical Chemistry*, 1992; vol. 64, No. 22, pp. 2672–2677.

U.S. Appl. No. 09/710,184, Bedingham et al., filed Nov. 10, 2000.

U.S. Appl. No. 09/841,264, Parthasarathy et al., filed Apr. 24, 2001.

U.S. Appl. No. 09/841,272, Parthasarathy et al., filed Apr. 24, 2001.

U.S. Appl. No. 09/894,810, Bedingham et al., filed Jun. 28, 2001.

U.S. Appl. No. 60/214,508, filed Jun. 28, 2000.
U.S. Appl. No. 60/214,642, filed Jun. 28, 2000.
U.S. Appl. No. 60/237,072, filed Oct. 2, 2000.
U.S. Appl. No. 60/260,063, filed Jan. 6, 2001.
U.S. Appl. No. 60/284,637, filed Apr. 18, 2001.
U.S. Appl. No. 09/895,001, Harms et al., filed Jun. 28, 2001.
U.S. Appl. No. 09/895,010, Bedingham et al., Jun. 28, 2001.
U.S. Appl. No. 10/027,226, Parthasarathy et al., filed Dec. 20, 2001.

* cited by examiner

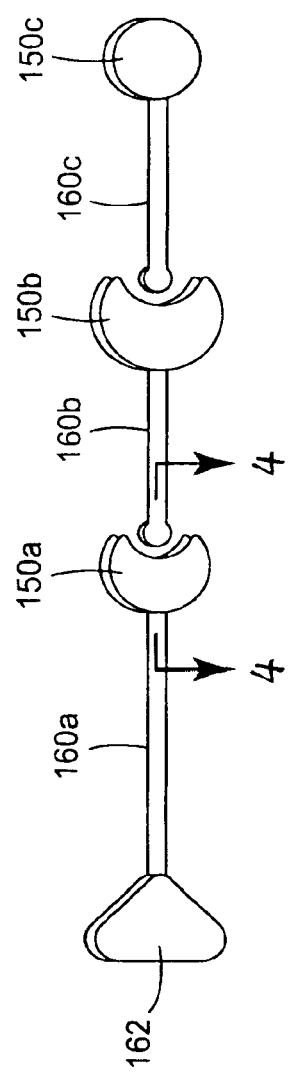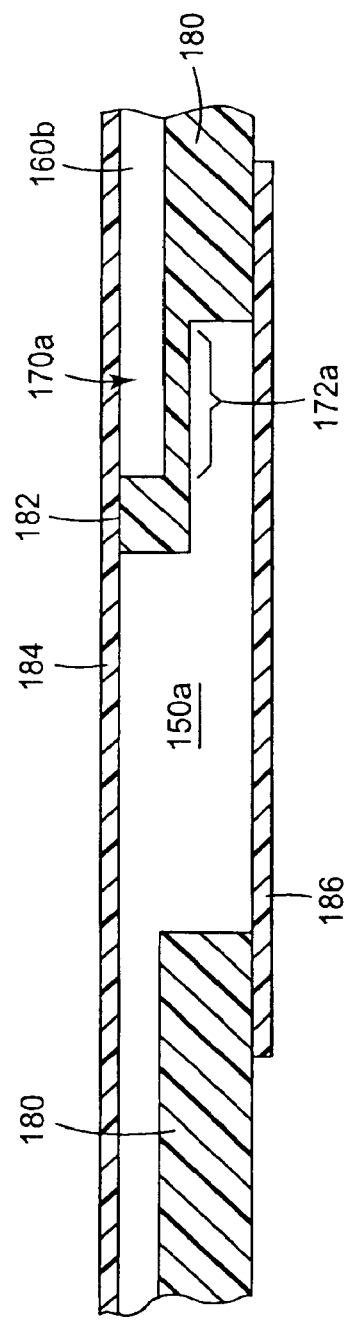

METHODS AND DEVICES FOR REMOVAL OF ORGANIC MOLECULES FROM BIOLOGICAL MIXTURES USING ANION EXCHANGE

BACKGROUND

Water-soluble dyes (e.g., fluorescent, chemiluminescent, visible, and near-IR) are used routinely in molecular biology to label and monitor components of biological reactions. Frequently, residual dyes as well as other organic molecules should be removed before proceeding with many downstream applications. Thus, the present invention is directed to removing dyes and other organic molecules from biological mixtures, particularly in low volume, microfluidic devices.

There is a significant need for high throughput, low volume, integrated microfluidic devices in order to increase sample throughput and reduce the amount of reagents used per sample (thereby reducing cost per sample) in biological reactions. Small volume Polymerase Chain Reaction (PCR) and nucleic acid cycle sequencing reactions are examples of standard molecular biology techniques that are suitable for incorporation into miniaturized formats. In both applications, removal of residual primers, nucleic acid templates, dyes, and other organic molecules are generally necessary prior to any further downstream applications.

One example where such removal methods are used is in the preparation of a finished sample (e.g., purified nucleic acid materials) from a starting sample (e.g., a raw sample such as blood, bacterial lysate, etc.). For example, to obtain a purified sample of the desired materials in high concentrations, the starting sample is typically prepared for PCR after which the PCR process is performed to obtain a desired common PCR reaction product. The common PCR reaction product can then be used in a variety of molecular biological applications, including, for example, sequencing, cloning, genotyping, and forensic applications.

In fluorescence-based DNA sequencing applications, unincorporated dye terminators (i.e., dye-labeled dideoxy terminators such as dideoxynucleotide triphosphates (ddNTPs)) should preferably be removed from the reaction mixture prior to analysis of the DNA sequence fragments. Failure to sufficiently reduce the concentration of dye terminator molecules leads to dye artifacts (i.e., other dye-containing molecules such as dye-labeled dideoxy terminators such as dideoxynucleotide diphosphates (ddNDPs), dideoxynucleotide monophosphates (ddNMPs), and dideoxynucleosides) that can significantly obscure DNA sequence information. Sequencing reaction purification is a desired step in the preparation of samples prior to sequence analysis, particularly when using a capillary electrophoresis (CE) sequencer.

Conventionally, after completion of the PCR or cycle sequencing reaction, the product is generally purified by either alcohol (ethanol or isopropanol) precipitation or gel filtration chromatography. Other protocols using polyalkylene glycol and biotin-streptavidin interactions have also been utilized for sequencing reaction clean-up. Ultrafiltration membranes, phenol/chloroform extraction, and enzymatic treatments are other methods that are commonly used for purification of PCR and sequencing reaction mixtures.

Such conventional technologies for the purification of PCR and nucleic acid sequencing reactions have not proven to be suitable for incorporation into a microfluidic device. Alcohol precipitation utilizes volatile and flammable reagents. Hydrogels (e.g., crosslinked dextrans), commonly used in size exclusion chromatography, require large bed volumes (10× relative the volume of sample) for efficient separation of impurities from product. Gels are first swollen with a relatively large volume of water, centrifuged, and loaded substantially immediately, because, upon dehydration, these materials are prone to cracking. Biotin-streptavidin mediated purifications require the use of custom biotinylated primers for the efficient capture of product. Biotinylated products are generally captured onto streptavidin-treated paramagnetic particles and physically separated from impurities with the use of a magnet. Alternatively, hybridization based purification (HBP) of the PCR or nucleic acid sequencing product can be accomplished by utilizing primers containing specially designed capture tags. Separation of the nucleic acid fragment from the biological matrix can be achieved by hybridization of the capture tag to a complementary strand bound to a solid support. Both the biotin and HBP strategies would require a rinsing step followed by elution of the sequencing or PCR product from the substrate. Although biotin-streptavidin and HBP purification methods yield clean PCR and sequencing fragments, both approaches require customized primers, which can be cumbersome and expensive.

An alternative approach for the removal of residual dye terminators from DNA sequencing reactions involves treating the reaction mixture with an enzyme (e.g., shrimp alkaline phosphatase) to dephosphorylate residual nucleotide triphosphates. Although cleavage of the phosphate groups(s) from the dye-labeled dideoxynucleotide triphosphates alters the mobility of the dye-labeled nucleotides in the sequencing gel, residual dye moieties are not removed from the reaction mixture by this procedure and must still be eliminated prior to injection of the sample into the sequencer. This is generally accomplished by subsequent alcohol precipitation of the digested product.

PCR and sequencing products can also be effectively purified by adsorption of nucleic acid fragments onto beads and silica gel membranes using chaotropic agents. Impurities (e.g., residual primers, dyes, and salts) can be rinsed from the substrate and the purified product eluted. This multi-step bind/rinse/elute purification scheme may also prove to be cumbersome within the context of a microfluidic device.

Yet another method of removing unwanted materials (e.g., dyes) from cycle sequencing (e.g., Sanger cycling) reaction mixtures involves the use of paramagnetic particles. One example of suitable paramagnetic particles incorporating dye terminator removal materials is available under the trade designation RAPXTRACT from Prolinx Inc., Bothell, Wash. Further examples of these materials (and their methods of use) may be found in U.S. patent application Ser. No. 09/894,8 10 filed on Jun. 28, 2001 and entitled ENHANCED SAMPLE PROCESSING DEVICES SYSTEMS AND METHODS (U.S. Pat. Application Publication No. 2002/0047003 A1 (Bedingham et al.)). Unfortunately, however, with such particles, the particles must remain in a hydrated state, which limits the ability to prefabricate particle-loaded devices.

Thus, methods are needed for the removal of dyes and other organic molecules from biological mixtures, such as nucleic acid amplification reaction mixtures (e.g., PCR or cycle sequencing reaction mixtures).

SUMMARY OF THE INVENTION

The present invention provides methods for processing biological mixtures, i.e., samples containing a biological material such as peptide- and/or nucleotide-containing material. Specifically, the present invention provides methods for the removal of negatively charged organic molecules (e.g., dyes, primers, probes, dNTPs, dye terminators such as ddNTPs, ddNDPs, ddNMPs, and nucleosides) from biological sample mixtures using anion exchange materials. These methods are based on solid-phase extraction techniques. They are advantageous because they can be incorporated into high throughput, low volume, integrated microfluidic devices, if desired, particularly those being developed for PCR and DNA sequencing.

The present invention provides methods of removing small negatively charged organic molecules from a biological sample mixture. Preferably, the biological sample mixture is a biological sample mixture such as a nucleic acid amplification reaction mixture (e.g., a PCR reaction mixture or a nucleic acid sequencing reaction mixture).

Herein, "removal" of unwanted molecules involves adhering such molecules to the solid-phase material and allowing desirable products to remain in solution. This is in contrast to conventional elution methods that involve adhering the desirable products to the solid-phase material, washing away the unwanted molecules, and eluting the desirable products to remove them from the solid-phase material.

In one embodiment, a method includes: providing a surface that includes an anion exchange material; providing a biological sample mixture comprising small negatively charged organic molecules having a molecular weight of less than about 6,000; wherein the biological sample mixture is selected from the group consisting of a nucleic acid amplification reaction mixture (e.g., a PCR reaction mixture or a sequencing reaction mixture) and a nucleic acid labeling reaction mixture; and contacting the biological sample mixture with the surface that includes the anion exchange material to remove at least a portion of the small negatively charged organic molecules from the biological sample mixture.

In another embodiment, a method includes: providing a surface that includes an anion exchange material (preferably, including quaternized nitrogen-containing groups such as quaternary ammonium ions) partially coated with a negatively charged polymer (preferably, a polyelectrolyte); providing a biological sample mixture; and contacting the biological sample mixture with the surface that includes an anion exchange material partially coated with a negatively charged polymer to remove at least a portion of the small negatively charged organic molecules from the biological sample mixture.

In another embodiment, a method includes: providing a device (e.g., a microfluidic device) that includes at least one process array that has a surface that includes an anion exchange material; providing a biological sample mixture in the at least one process array, wherein the biological sample mixture includes small negatively charged organic molecules having a molecular weight of less than about 6,000; and transferring the biological sample mixture within the at least one process array, wherein the biological sample mixture and the surface having an anion exchange material remain in contact for a sufficient time to remove at least a portion of the small negatively charged organic molecules from the biological sample mixture.

In yet another embodiment, a method includes: providing a device that includes at least one process array that has a surface including an anion exchange material (preferably, quaternary ammonium ions) partially coated with a negatively charged polymer (preferably, a polyelectrolyte); providing a biological sample mixture in the at least one process array; and transferring the biological sample mixture within the at least one process array, wherein the biological sample mixture and the surface including an anion exchange material partially coated with a negatively charged polymer remain in contact for a sufficient time to remove at least a portion of the small negatively charged molecules from the biological sample mixture.

When the biological sample mixture is a sequencing reaction mixture, the small negatively charged molecules are typically selected from the group consisting of dye-labeled terminators, primers, degraded dye molecules, deoxynucleotide triphosphates, and mixtures thereof. Preferably, for such a sample, the method is carried out under conditions effective to remove substantially all the dye-labeled terminators from the biological sample mixture.

When the biological sample mixture is a PCR reaction mixture, the small negatively charged molecules are typically selected from the group consisting of primers, degraded dye molecules, deoxynucleotide triphosphates, and mixtures thereof. Preferably, for such a sample, the method is carried out under conditions effective to remove substantially all the primers from the biological sample mixture.

The present invention also provides devices that can be used to carry out methods of the present invention. Such devices include analytical receptacles, such as microfluidic devices and microtiter plates, for example.

In one embodiment, a device includes: a plurality of process arrays that include: a plurality of process chambers, each of the process chambers defining a volume for containing a biological sample mixture; and at least one distribution channel connecting the plurality of process chambers; a surface within at least one of the process arrays that includes an anion exchange material (preferably, quaternary ammonium ions). Preferably, the device further includes a plurality of valves, wherein at least one of the valves is located along the at least one distribution channel. Preferably, in the device, the surface that includes an anion exchange material also includes an anion exchange material partially coated with a negatively charged polymer (preferably, a polyelectrolyte). Preferably, the anion exchange material and/or the negatively charged polymer are pattern coated.

In yet another embodiment of the device, the present invention provides an analytical receptacle that includes one or more reservoirs and a surface with a cover film adhered to the surface and enclosing the one or more reservoirs; wherein the cover film includes a backing and an adhesive disposed on at least one major surface of the backing and in contact with the receptacle surface; wherein at least a portion of the adhesive has an anion exchange material (preferably, quaternary ammonium ions) disposed thereon. Preferably, the anion exchange material is partially coated with a negatively charged polymer (preferably, a polyelectrolyte). Preferably, the anion exchange material and/or the polymer are pattern coated.

In still another embodiment, there is provided an analytical receptacle that includes a plurality of reservoirs adapted for receipt of a biological sample mixture, wherein at least one reservoir includes a surface that includes an anion exchange material (preferably, quaternary ammonium ions) partially coated with a negatively charged polymer (preferably, a polyelectrolyte) disposed therein.

These and other features and advantages of the methods of the invention are described below with respect to illustrative embodiments of the invention.

BRIEF DESCRIPTION OF THE DRAWINGS

FIG. 3 is an enlarged view of one process array on the device of FIG. 2.

FIG. 4 is a cross-sectional view of a portion of the process array of FIG. 3, taken along line 4—4 in FIG. 3.

DETAILED DESCRIPTION OF PREFERRED EMBODIMENTS

Figure 1:
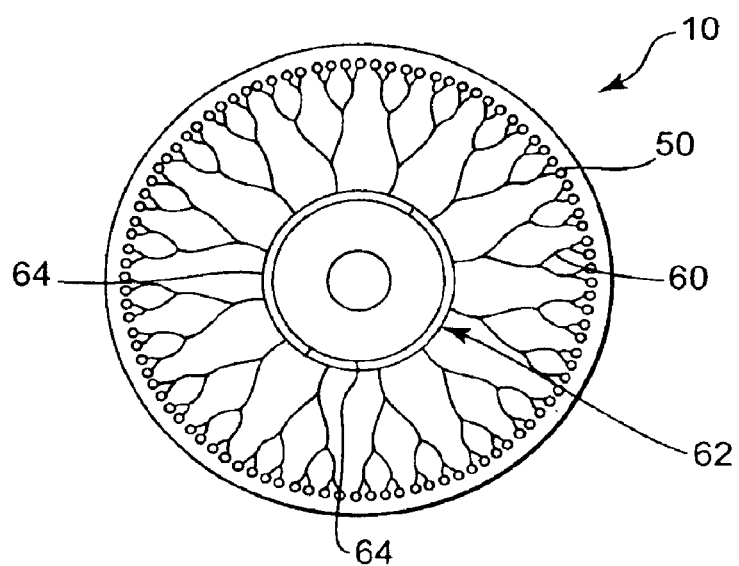
FIG. 1 is a top plan view of one device that can be used in connection with the present invention.

The methods of the present invention utilize solid-phase extraction techniques for processing biological sample mixtures to remove at least a portion of small organic molecules (e.g., molecules having a molecular weight of less than about 6,000) included in such mixtures. These small molecules are typically negatively charged and the solid-phase extraction material is typically an anion exchange material. The biological sample mixture (i.e., a sample containing a biological material such as peptide- and/or nucleotide-containing material) is preferably a biological reaction mixture (e.g., a PCR or cycle sequencing or other nucleic acid amplification reaction mixture). The small organic molecules are preferably residual or unincorporated materials (including degradation products) in biological reactions (e.g., dyes, primers, probes, dNTPs, dye terminators such as ddNTPs, ddNDPs, ddNMPs, and nucleosides). Significantly, using the solid-phase extraction materials of the present invention, the undesirable molecules preferably preferentially adhere to the solid-phase material and the desirable products remain in the biological sample solution.

Examples of nucleic acid amplification reaction mixtures suitable for use in the present invention include, but are not limited to: a) polymerase chain reaction (PCR); b) target polynucleotide amplification methods such as self-sustained sequence replication (3SR) and strand-displacement amplification (SDA); c) methods based on amplification of a signal attached to the target polynucleotide, such as branched chain DNA amplification; d) methods based on amplification of probe DNA, such as ligase chain reaction (LCR) and QB replicase amplification (QBR); e) transcription-based methods, such as ligation activated transcription (LAT) and nucleic acid sequence-based amplification (NASBA); f) cycle sequencing reactions such as Sanger sequencing; and g) various other amplification methods, such as repair chain reaction (RCR) and cycling probe reaction (CPR).

Such methods are particularly desirable for use in the clean-up of PCR reaction mixtures, nucleic acid sequencing reaction mixtures, nucleic acid labeling reaction mixtures, or hybridization reaction mixtures, particularly PCR, nucleic acid sequencing, and nucleic acid labeling reaction mixtures, and more particularly PCR or nucleic acid cycle sequencing or other nucleic acid amplification reaction mixtures. That is, the methods of the present invention are particularly desirable for removing residual reactants and degradation products thereof (e.g., undesirable dye-containing molecules such as ddNDPs and the like) from the desired nucleic acid amplification reaction products (e.g., PCR or sequencing reaction products). The removal of residual dyes (including near-IR, fluorescent, chemiluminescent, UV, and visible) or undesirable dye-containing molecules and other small organic molecules may be important in numerous other genomics and proteomics applications as well (e.g., ligation reactions and protein or peptide affinity binding reactions).

These methods are based on solid-phase extraction techniques, and can be desirably incorporated into high throughput, low volume, integrated microfluidic devices, particularly those being developed for PCR and DNA sequencing. Some desirable qualities of a solid-phase extraction method for PCR or DNA sequencing reaction clean-up for use in an integrated microfluidic device include, for example: 1) the use of high surface area to bed volume ratio porous or nonporous materials that can be incorporated into a spin column, titer well plate, or a well or channel within a flow-through microfluidic device; 2) the use of non-hydrogel based materials that do not require hydration/swelling and are not prone to cracking upon dehydration; 3) no need for specially designed primers or multi-step binding/rinsing/elution protocols; 4) no volatile or corrosive solvents; 5) no leachables that could contaminate DNA products or compromise the structure of the device; and 6) the ability to remove dyes and other residual reactants while not removing a significant amount of PCR or sequencing reaction products.

The methods of the present invention use anion exchange materials effective for selective removal of negatively charged small molecules (e.g., molecules having a molecular weight less than about 6,000, such as dye terminators), while retaining the larger product molecules (e.g., sequencing ladders), which are often negatively charged as well. Herein, "small organic molecules" refer to molecules in a biological sample mixture, such as a PCR or sequencing reaction mixture or other nucleic acid amplification reaction mixture, that are not the desired product molecules. Typically, the small organic molecules that are removed from biological sample mixtures are smaller than the desired products. Preferably, the small organic molecules that are removed from biological sample mixtures have a molecular weight of less than about 6,000. Such small molecules tend to adhere (i.e., adsorb, absorb, or otherwise bind) to the solid-phase extraction materials of the present invention, whereas molecules with a molecular weight of greater than about 8,000 generally do not. For molecules of intermediate molecular weight, the smaller the molecule, the greater the tendency to adhere (i.e., adsorb, absorb, or otherwise bind), whereas the larger the molecule, the less the tendency to adhere (i.e., adsorb, absorb, or otherwise bind). Typically, the desired PCR amplicons have greater than about 50 base pairs and molecular weights of greater than about 33,000. Typically, the desired sequencing ladders have greater than about 18 bases and molecular weights of greater than about 6,000.

Preferably, the anion exchange materials include a surface having bound quaternized nitrogen-containing groups such as quaternary ammonium ions. These quaternary ammonium ions, for example, are typically charge balanced with chloride ions, although other anions can be used for charge balancing and exchange such as iodide, fluoride, nitrate, bisulfite, cyanide, bicarbonate, hydroxide, sulfate, and the like. The concentration of such ions can be tailored for the desired result. For example, for certain methods described herein, the anion exchange materials preferably include at least about 0.01 micromole active groups (e.g., quaternary ammonium ions measured as the amount of chloride) per 1735 $mm^2$ surface area, more preferably, at least about 10 micromoles active groups per 1735 $mm^2$ surface area, and even more preferably, at least about 20 micromoles active groups, per 1735 $mm^2$ surface area, prior to further treatment (e.g., passivation). There is no upper limit to the number of active groups on an anion exchange material for the present invention. This is typically controlled by what is commercially available. Typically, they include no more than about 1000 micromoles active groups (e.g., quaternary ammonium ions measured as the amount of chloride) per 1735 mm$^2$ surface area, and more often, no more than about 200 micromoles active groups per 1735 mm$^2$ surface area, prior to further treatment (e.g., passivation).

Although the anion exchange material preferably includes quaternary ammonium ions, other positively charged ions can be used, particularly those including quaternized nitrogen atoms. Preferred materials include strong anion exchangers having a fixed positive charge (i.e., the ions are positively charged regardless of pH, and particularly at a pH of 8–9). These include, for example, quaternary ammonium anion exchangers (such as those commercially available under the trade designation AMBERLITE, Type I, from Supelco, Bellefonte Pa.), quaternary alkylamine anion exchangers (such as those commercially available under the trade designation DIAION, Type I, from Supelco), trimethylbenzyl ammonium anion exchangers (such as those commercially available under the trade designation DOWEX, Type I, from Supelco), dimethylethanolamine anion exchangers (such as those commercially available under the trade designation AMBERLITE, Type II, from Supelco), quaternary alkylalkanolamine anion exchangers (such as those commercially available under the trade designation DIAION, Type II, from Supelco), and dimethylethanolbezyl ammonium anion exchangers (such as those commercially available under the trade designation DOWEX, Type II, from Supelco). Furthermore, weak anion exchangers could also be used in the present invention if there are a significant number of positively charged species under conditions of use (e.g., at less than pH 7). These include polyamines (such as those commercially available under the trade designations AMBERLITE, DOWEX, and DUOLITE from Supelco) and alkylamines (such as those commercially available under the trade designation DIAION).

A variety of solid-phase extraction materials, preferably including quaternary ammonium groups, are commercially available. In addition to those listed above, suitable commercially available materials include, for example, ion exchange microporous membranes. One such commercially available membrane is available under the trade designation SB-6407 from Pall Corp., East Hills, N.Y., which is a strongly basic positively charged polyethersulfone (PES)/copolymer membrane treated to have ion-exchange capacity on the outer surfaces. The ion-exchange capacity is provided by quaternary ammonium active sites. Such a filter is supplied in the chloride ion form, and has a pore size of about 0.45 micrometer (i.e., micron or µ or µm), a thickness of about 150 micrometers, and an ion exchange capacity of about 20 microequivalents per 3470 square millimeter (mm$^2$) surface area, prior to further treatment (e.g., passivation).

Suitable solid-phase extraction materials can be prepared using a variety of techniques. For example, quaternary ammonium groups can be covalently attached to an underlying substrate (e.g., even as thin as a monolayer), using, for example, a quaternary ammonium functionalized material such as a silane. Alternatively, an amine-containing polymer, such as a polyalkylene imine (e.g., polyethylene imine), can be treated with a quaternizing agent, such as methyl iodide, to form quaternary ammonium ion groups on an underlying substrate. If desired, the polyalkylene imine can be crosslinked prior to quaternization.

In yet another approach, a water-soluble or water-insoluble polyquat (i.e., a polymer containing quaternary ammonium ion groups) can be coated on a substrate with or without subsequent crosslinking. Suitable water-soluble polymers include poly(diallyldimethylammonium chloride), poly(2-hydroxy-3-methacryloxypropyl trimethylammonium chloride), and poly(butylacrylate-methacryloxyethyl trimethylammonium bromide), for example. Suitable water-insoluble polymers include quaternary acrylic copolymers such as those commercially available under the trade designations SYNTRAN Hx31-65 (trimethyl aminoethyl methacrylate and methyl methacrylate) and SYNTRAN Hx31-44 (1-methoxy-2-propanol acrylate copolymer) from Interpolymer Corp., Canton, Mass.

The anion exchange material can be crosslinked if desired, particularly if it is water soluble. For example, crosslinking methods that could be used to crosslink the anion exchange material, or precursors thereof, include the application of heat, ultraviolet (uv) of electron-beam (e-beam) radiation, or chemical methods. For example, a polyquat can be crosslinked by using a heat activated chemical crosslinker such as polyfunctional glycidyl ether (e.g., phenyl glycidyl ether, butyl glycidyl ether). Alternatively, passivation methods can render the water-soluble materials water insoluble (e.g., by precipitation).

If desired, the anion exchange materials can also include additives such as plasticizers to enhance the flexibility of films formed therefrom. Examples include gelatin and dibutyl phthalate.

Anion exchange materials (e.g., surfaces with bound quaternary ammonium ion groups) without further treatment (e.g., passivation) can be used in separation methods of the present invention, although they are generally nonselective. That is, they will remove the desired product (e.g., DNA sequencing ladders) as well as the undesired small molecules (e.g., dye terminators). If the concentration of the desired product is sufficiently large in a sample mixture, although the recovery would be quite low, it may be suitable for certain applications.

Preferably and advantageously, however, the anion exchange materials (e.g., bound quaternary ammonium ions) are partially coated with a negatively charged polymer, preferably a negatively charged polyelectrolyte. This partial passivation of the positive charges of the anion exchange material (e.g., quaternary ammonium ion groups) by the negatively charged polymer results in the remaining positively charged sites to be available for binding of small molecules through exchange with the counterions (typically with chloride ions). As a result, the surface is more selective, which provides better recovery as well as reproducibility. Significantly, passivation can also render water-soluble anion exchange materials suitable for use with aqueous sample mixtures, for example, by anion exchange and precipitation.

Suitable negatively charged polymers include those with multiple charges per molecule or with one or more charged end groups. For example, the negatively charged polymer can be a polyalkylene oxide (preferably, polyethylene oxide, polypropylene oxide, polyethylene-propylene oxide) with a negatively charged end group such as a carboxylate, as well as silanes and polyethylene glycol silanes functionalized with a negatively charged end group.

Preferred negatively charged polymers are molecules, typically macromolecules, in which a substantial portion of the constitutional units carry a charge when dissolved in an ionizing solvent. Suitable negatively charged polyelectrolytes are those that typically have molecular weights above 10,000, and preferably have low non-specific binding to components in a biological mixture. Suitable examples include a polystryene sulfonic acid (e.g., poly(sodium 4-styrenesulfonate) or PSSA), polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, and salts or other derivatives thereof. Various combinations of these can be used if desired.

The negatively charged polymer (e.g., polyelectrolyte) is present on the anion exchange material such that it only partially (i.e., not completely) blocks the positively charged species. Preferably, it is present in an amount of at least about 0.015 microgram (μg), and more preferably, at least about 0.03 milligram (mg), per 1735 mm$^2$ surface area. The upper limit to the amount of negatively charged polymer is dependent on the number of active groups in the anion exchange material. Generally, there is no upper limit as long as all the active anion exchange groups are not blocked by the polymer, i.e., are still available for binding of small molecules. Typically, a polymer is present on the anion exchange material in an amount of no greater than about 5 mg per 1735 mm$^2$ surface area, and more often, no greater than about 1 mg per 1735 mm$^2$ surface area, although it could be much higher (e.g., 100 mg per 1735 mm$^2$ surface area).

The negatively charged polymer is typically applied as an aqueous solution to the anion exchange material (e.g., surface having bound quaternary ammonium ion groups thereon). The preferred challenge concentration (i.e., the concentration of the solution) of the negatively charged polymer is chosen to provide maximum recovery of the desired product (e.g., DNA), preferably with substantially complete removal of dye-containing small organic molecules. Typically, it has been found that a challenge concentration of at least about 0.0001 percent by weight (wt-%) in deionized water (for a sample of material being coated having about 434 mm$^2$ surface area) provides suitable recovery values. Increasing recovery generally occurs with higher challenge concentrations; however, when the challenge concentration exceeds a threshold value (e.g., 1.0 wt-% for a sample of material being coated having about 434 mm$^2$ surface area), dye-containing small organic molecules can be incompletely removed. Although this results in good signal intensity, poor quality of sequencing chromatograms, for example, can occur.

In addition to improving product (e.g., DNA) recovery, passivation with the negatively charged polymer can alter the time taken for sample processing (e.g., PCR or sequencing reaction mixture clean-up). For example, in the case of commercially available PES membranes, higher challenge concentrations (e.g., higher than about 0.03 wt-% for a sample being coated having about 434 mm$^2$ surface area) of a polymer such as a polyelectrolyte can result in longer times for substantially complete removal of dye-containing small organic molecules. Relatively long processing (e.g., cleanup) times (e.g., about 10–15 minutes) can be useful for manual processing of many sample mixtures; however, in a microfluidic device, it is advantageous to reduce processing times. Thus, lower challenge concentrations (e.g., no greater than about 0.005 wt-% for a sample being coated having about 434 mm$^2$ surface area) of a polymer such as a polyelectrolyte are preferred for such applications.

The anion exchange material (e.g., material containing quaternary ammonium ion groups) and particularly the anion exchange material partially coated with a negatively charged polymer (e.g., a polyelectrolyte) (all of which are referred to herein as the "active chemistry") can be applied to the surfaces of a variety of substrates. Suitable substrates include beads, membranes, adhesive-coated articles, frits, foams, gels, microreplicated articles, or on the walls of a channel/well of an analytical receptacle. Substrates with higher surface areas enhance contact area, which can improve processing efficiency. The substrate can be treated for improved adhesion/surface area by a variety of treatments such as oxygen plasma, diamond-like glass deposition, corona treatment, e-beam or uv radiation, heat, as well as other similar techniques.

Such substrates can be porous and nonporous; however, porous materials have the advantage of large surface area to bed volume ratios and are particularly useful in flow-through applications. Suitable materials include high surface area organic and inorganic materials, which are routinely used in adsorption chromatography for decolorizing synthetic reactions.

Inorganic materials include, for example, silica gel, alumina, zirconia, and diatomaceous earth. Molecular sieves, such as zeolites (i.e., sodium and calcium aluminosilicates), can also be used in a similar fashion. Zeolites have the additional advantage that they can selectively trap small ionic species within their pores based on size. Porous ceramic particles and membranes (alumina, zirconia, silica, and aluminosilicate) can also be used.

Organic materials include, for example, oligosaccharides, polyesters, polysulfones, polycarbonates, polyvinyl chlorides, polyvinyl acetates, polymethyl methacrylates, cellulose esters, polyesters, and the like. Many other organic materials can be used, which are typically available in the form of membranes, films, or particles.

The anion exchange materials, particularly when partially coated with a negatively charged polymer (e.g., a polyelectrolyte), provide sites for relatively strong binding of the undesirable small organic molecules (e.g., dye terminators) while repelling larger negatively charged product molecules (e.g., DNA sequencing ladders) based on charge and size effects, thereby allowing for selective cleanup.

The anion exchange materials, preferably the polymer-coated anion exchange materials, can be used effectively for purification of nucleic acid amplicons after the polymerase chain reaction (PCR), for example. As is well known, PCR allows for analysis of extremely small amounts of nucleic acid (e.g., DNA). Briefly, a nucleic acid molecule (e.g., DNA template) is repeatedly synthesized using a polymerase enzyme (such as Taq DNA polymerase), an excess of two oligonucleotide primers (capable of flanking the region to be amplified and acting as a point of initiation of synthesis when placed under conditions in which synthesis of a primer extension product that is complementary to a target nucleic acid strand is induced), and free deoxynucleotide triphosphates (dNTPs, e.g., dGTP, dATP, dCTP and dTTP), which results in the amplification of a particular sequence by a millionfold or more. The resultant extension or amplification products are typically referred to as "PCR products" or "PCR amplicons."

Preferably, the PCR products incorporate a detectable label or tag, as can other materials in the PCR reaction mixture (e.g., primers and dNTPs). Thus, PCR amplification of target nucleic acid is preferably accomplished by utilizing at least one primer containing a detectable tag. For example, ultraviolet, visible, or infrared absorbing tags could be used that would produce specific ultraviolet, visible, or infrared signals. Examples of a wide variety of tags (a chemical moiety that is used to uniquely identify a nucleic acid of interest) are disclosed in International Publication No. WO 97/27325. Particularly preferred such tags are fluorescent or chemiluminescent agents. These are typically dye compounds that emit visible radiation in passing from a higher to a lower electronic state, typically in which the time interval between adsorption and emission of energy is relatively short, generally on the order of about $10^{-8}$ to about $10^{-3}$ second. Suitable fluorescent or chemiluminescent compounds can include fluorescein, rhodamine, luciferin, as well as a wide variety of others known to one of skill in the art.

In clean-up of PCR reaction mixtures after PCR has occurred, the undesired negatively charged small molecules include residual primers (labeled or unlabeled), degraded dye molecules (i.e., dye molecules or fragments thereof severed from the dye-labeled primers), and dNTPs (labeled or unlabeled). Of these molecules it is particularly important to remove the primers.

Preferably, using the methods of the present invention at least a portion of one or more of these unincorporated materials can be separated from the PCR products (i.e., removed from the PCR reaction mixture). Typically, the smaller molecules are removed (e.g., dNTPs) more easily than the larger molecules (primers). More preferably, at least about 90% of the residual primers and/or at least about 70% of the dNTPs are removed from a PCR reaction mixture using the methods of the present invention. Even more preferably, substantially all (i.e., at least about 95%) of one or more of the residual primers, degraded dye molecules, and dNTPs, are separated from the desired PCR products. Most preferably, substantially all (i.e., at least about 95%) of all the residual primers, degraded dye molecules, and dNTPs, are separated from the desired PCR products. The level of removal of primers can be determined by the OLIGREEN ssDNA quantitation reagent (Molecular Probes, Eugene, Oreg.), high pressure liquid chromatography (HPLC), and capillary electrophoresis (CE). The level of removal of dNTPs can be determined by absorbance at 1260 nm, HPLC, and CE.

Preferably, using the methods of the present invention, at least about 30% of the desired PCR product (e.g., DNA amplicon) is recovered from a PCR reaction mixture. More preferably, at least about 50% of the desired PCR product is recovered from a PCR reaction mixture. Even more preferably, at least about 70% of the desired PCR product is recovered from a PCR reaction mixture. Most preferably, at least about 90% of the desired PCR product is recovered from a PCR reaction mixture. The level of PCR product recovery can be determined by Agilent 2100 Bioanalyzer available from Agilent Technologies, Palo Alto, Calif.

For certain methods of PCR reaction mixture clean-up, the anion exchange materials preferably include at least about 10 micromoles, and often up to about 200 micromoles, active groups (e.g., quaternary ammonium ions measured as the amount of chloride) per 1735 $mm^2$ surface area, prior to further treatment (e.g., passivation). The passivation level (i.e., the level of negatively charged polymer (e.g., polyelectrolyte)) is generally at least about 0.03 mg, and often up to about 30 mg, per 1735 $mm^2$ surface area and typically no greater than 5 mg per 1735 $mm^2$. Challenge concentration of the passivating polymer is typically 2–3 times higher for PCR than for sequencing. The clean-up is preferably carried out at room temperature, although higher temperatures could be used if desired. A typical time for clean-up is less than about 5 minutes.

These anion exchange materials, preferably the polymer-coated anion exchange materials, can also be used effectively for purification of nucleic acid (e.g., DNA) sequencing ladders after, for example, Sanger cycling. As is well known, sequencing, such as Sanger sequencing, produces a nested set of fragments from a template strand (e.g., a DNA template) by replicating the template strand to be sequenced. Briefly, a nucleic acid molecule (e.g., DNA template) of unknown sequence is combined with a nucleic acid polymerase, a primer, free deoxynucleotide triphosphates (dNTPs, e.g.,dGTP, dATP, dCTP and dTTP), and one of the four free dideoxynucleotide triphosphates (a dideoxynucleotide cannot bond to other nucleotides because its 3' end is modified, thus, when dideoxynucleotides are incorporated, strand synthesis stops) to produce a random sample of varying length segments of nucleic acid. Thus, sequencing mixtures contain salts, enzymes, unincorporated deoxynucleotide triphosphates (dNTPs), template nucleic acid, primers, and the resultant nucleic acid sequencing ladders. Various of these materials (e.g., primers and dNTPs) can be labeled with dye molecules or unlabeled. Such mixtures also include unincorporated dye-labeled dideoxynucleotide terminators such as dye-labeled dideoxynucleotide triphosphates (ddNTPs), which can be hydrolyzed (e.g., treated enzymatically with a phosphatase such as shrimp alkaline phosphatase to dephosphorylate residual nucleotide triphosphates) to form dye-labeled artifacts such as dye-labeled dideoxynucleotide diphosphates (ddNDPs), dye-labeled dideoxynucleotide monophosphates (ddNMPs), and dye-labeled dideoxynucleosides. As described in International Publication No. WO 01/25490, such unincorporated dye-labeled terminators typically have to be removed from the DNA sequencing ladders prior to electrophoresis. Herein, the "dye-labeled terminators" are also referred to as "dye terminators" and include ddNTPs, ddNDPs, ddNMPs, and dideoxynucleosides. Particularly preferred such dyes are fluorescent or chemiluminescent agents and include fluorescein, rhodamine, luciferin, etc.

In clean-up of sequencing reaction mixtures after cycling has occurred, the undesired negatively charged small molecules include residual primers (labeled or unlabeled), degraded dye molecules (i.e., dye molecules or fragments thereof severed from the dye-labeled terminators), dNTPs (labeled or unlabeled), and dye terminators. Of these, it is particularly important to remove the dye terminators. Preferably, using the methods of the present invention at least a portion of one or more of these unincorporated materials can be separated from the sequencing products (i.e., removed from the sequencing reaction mixture). Typically, the smaller molecules are removed (e.g., dNTPs) more easily than the larger molecules (primers) and the more highly charged molecules are removed more easily than the less highly charged molecules (e.g., the ease of removal decreases from ddNTPs to ddNDPs to ddNMPs to nucleosides). More preferably, substantially all (i.e., at least about 95%) of one or more of the residual primers, degraded dye molecules, dNTPs, and dye terminators are separated from the sequencing products. Most preferably, substantially all (at least about 95%) of all the residual primers, degraded dye molecules, dNTPs, and ddNTPs are separated from the sequencing products. Significantly and preferably, using the methods of the present invention, at least about 95%, more preferably, at least about 98%, and most preferably, 100%, of all the dye terminators are separated from sequencing products. Such products can then be analyzed by sequencing. The level of removal of dye terminators can be determined by fluorescence, CE, or HPLC.

Preferably, using the methods of the present invention, at least about 30% of the desired sequencing product (e.g., DNA ladder) is recovered from a cycle sequencing reaction mixture. More preferably, at least about 50% of the desired sequencing product is recovered from a cycle sequencing reaction mixture. Even more preferably, at least about 70% of the desired sequencing product is recovered from a cycle sequencing reaction mixture. Most preferably, at least about 90% of the desired sequencing product is recovered from a cycle sequencing reaction mixture. The level of product recovery can be determined by CE, for example.

For certain methods of sequencing reaction mixture cleanup, the anion exchange materials preferably include at least about 10 micromoles, and often up to about 200 micromoles, active groups (e.g., quaternary ammonium ions measured as the amount of chloride) per 1735 $mm^2$ surface area, prior to further treatment (e.g., passivation). The passivation level (i.e., the level of negatively charged polymer (e.g., polyelectrolyte)) is generally about 0.03 mg, and often up to about 30 mg, per 1735 $mm^2$ surface area and typically no greater than 5 mg per 1735 $mm^2$. The clean-up is preferably carried out at room temperature, although higher temperatures could be used if desired. A typical time for clean-up is less than about 5 minutes.

The active chemistry, particularly the polymer-coated anion exchange materials (e.g., the partially coated quaternary ammonium ion groups), can be incorporated into flow-through devices or non-flow-through formats. If a non-flow-through format is used, the reaction mixture can be incubated with or without mixing, preferably with mixing, for a given period of time and the resultant supernatant containing at least partially purified product (e.g., DNA amplicons) can be removed and analyzed.

Diffusion of small molecules to a surface having the active chemistry thereon can be improved by providing adequate mixing of the reactants. This can be accomplished by vortexing, shaking, heating, sonicating, etc. Providing intimate mixing can result in shorter times for processing (e.g., clean-up), better product recovery levels, and/or better reproducibility.

The active chemistry described herein, particularly the polymer coated anion exchange materials (e.g., the partially coated quaternary ammonium ion groups), can be incorporated into a variety of devices, particularly analytical receptacles. As used herein, analytical receptacles are devices that receive a sample, reagent, or solvent into one or more reservoirs, which may or may not designed for filtration. Examples include assay plate arrays (e.g., microtiter plates), discrete or continuous (e.g., strip or tape) structures containing a plurality of wells, channels, or other reservoirs, and arrays of the type used in 96-well filter plate assemblies (e.g., of the type described in U.S. Pat. No. 5,620,663 (Aysta et al.)).

Preferred analytical receptacles, without further modification, provide an open system of one or more reservoirs (e.g., wells or channels) to which fluids may be added directly. A cover film is typically applied along the length and width of an analytical receptacle to seal the receptacle, preferably the reservoir(s) of the receptacle, and create a closed system. Preferably, this results in producing individually sealed enclosures, which can be substantially continuous or discrete (i.e., discontinuous) structures.

A cover film, which acts as a sealing membrane, can include an adhesive, preferably, a pressure sensitive adhesive, disposed on a backing (preferably, a transparent backing). The adhesive is selected such that it adheres well to materials of which conventional analytical receptacles are made (preferably polyolefins, polystyrene, polycarbonate, or combinations thereof), maintains adhesion during high and low temperature storage (e.g., about −80° C. to about 200° C.) while providing an effective seal against sample evaporation, and does not substantially dissolve in or otherwise react with the components of the biological sample mixture. Thus, the type of adhesive is not critical as long as it does not interfere (e.g., bind DNA, dissolve, etc.) with the removal of unwanted materials from a biological sample mixture. Preferred adhesives include those typically used on cover films of analytical devices in which biological reactions are carried out. These include poly-alpha olefins and silicones, for example, as described in International Publication Nos. WO 00/45180 and WO 00/68336.

The active chemistry described herein can be incorporated into the analytical receptacle in a variety of ways. For example, it can be coated onto the walls of one or more reservoirs, it can be in the form of a flow-through membrane placed in one or more reservoirs, it can be coated on a film (which can be continuous or discontinuous or in the form of a plurality of pieces) placed in one or more reservoirs, or it can be coated on the adhesive of the adhesive-coated cover film. The active chemistry, either the anion exchange material (e.g., quaternary ammonium ions) or the negatively charged polymer or both, can be pattern coated.

The active chemistry described herein, particularly the polymer-coated anion exchange materials (e.g., the partially coated quaternary ammonium ion groups), is particularly well suited for use in a high throughput microfluidic device resulting in reagent and time savings, as well as elimination of the need to elute in the conventional sense (i.e., washing away the unwanted components from the bound desired products followed by removing the desired products). Such devices typically require low bed volume clean-up media for the purification of small volume reactions. The active chemistry can be incorporated into a microfluidic device in a variety of manners.

In one embodiment, an adhesive-coated cover film (or inner walls) of a microfluidic device can be coated with, preferably pattern coated with, the active chemistry (e.g., a polyquat followed by a PSSA solution). This coating, particularly pattern coating, can be accomplished by a variety of methods such as spray drying, dip coating, brush coating, knife coating, roll coating, ink-jet coating, screen printing, electrostatic deposition, etc. An unpurified biological sample mixture, e.g., a PCR or DNA sequencing reaction mixture, can be spun into a clean-up chamber containing the active chemistry on either or both the top and bottom surfaces of the chamber. The speed of this reaction can be enhanced by ensuring intimate contact of the solution with the chamber walls by mixing, vortexing, shaking, or through compression of the walls (made of a compliant material) of the device, etc. The purified reaction mixture is collected and ready for subsequent analysis (e.g., by injection into a DNA sequencing instrument).

In another embodiment, a solid-phase material having the active chemistry coated thereon can be positioned within a microfluidic compartment or channel. For example, a device having at least one process array that includes two connected process chambers, at least one of the process chambers and/or at least one volume defined by a connection (i.e., distribution channel) between at least two process chambers can include the solid-phase material. In this arrangement, if the solid-phase material is in the form of a porous material, an unpurified biological sample solution, e.g., PCR or DNA sequencing reaction mixture, passes through the solid-phase material, allowing sufficient residence time to trap the undesirable components (e.g., excess unincorporated dye terminators). Alternatively, if the solid-phase material is in the form of a nonporous material, the unpurified biological sample solution passes by the material. The contact area of the sample with the solid-phase material can be enhanced upon selection of a solid-phase material within larger surface area. The purified reaction mixture is collected and ready for subsequent analysis, such as occurs, for example, upon injection into a DNA sequencing instrument.

Although the methods of the present invention can be used in a variety of devices, a variety of illustrative embodiments of some suitable devices may be described in, e.g., U.S. patent application Ser. No. 09/894,810 filed on Jun. 28, 2001 and entided ENHANCED SAMPLE PROCESSING DEVICES SYSTEMS AND METHODS (U.S. Pat. Application Publication No. 2002/0047003 A1 (Bedingham et al.)). and U.S. patent application Ser. No. 09/895,010 filed on Jun. 28, 2001 and entitled SAMPLE PROCESSING DEVICES (U.S. Pat. Application Publication No. 2002/0064885 A1 (Bedingham et al.)). Other useable device constructions may be found in, e.g., U.S. Provisional Patent Application Ser. No. 60/214,508 filed on Jun. 28, 2000 and entitled THERMAL PROCESSING DEVICES AND METHODS; U.S. Provisional Patent Application Ser. No. 60/214,642 filed on Jun. 28, 2000 and entitled SAMPLE PROCESSING DEVICES, SYSTEMS AND METHODS; U.S. Provisional Patent Application Ser. No. 60/237,072 filed on Oct. 2, 2000 and entitled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METhODS; U.S. Provisional Patent Application Ser. No. 60/284,637 filed on Apr. 18, 2001 and titled ENHANCED SAMPLE PROCESSING DEVICES, SYSTEMS AND METHODS; and U.S. patent application Ser. No. 09/895,001 filed Jun. 28, 2001 and entitled SAMPLE PROCESSING DEVICES AND CARRIERS (U.S. Pat. Application Publication No. 2002/0048533 A1 (Harms et al.)).

The methods described herein can be used in a variety of different processes requiring at least partial removal of dyes or other organic molecules from biological reaction mixtures contained in the process arrays of microfluidic devices. Examples of such processes involve the clean-up of chemical reaction mixtures, e.g., nucleic acid amplification, which may or may not also be carried out in process arrays of the device. Some or all of the required reagents for anion exchange chemistry for clean-up (e.g., a polyquat partially coated with PSSA) may be present in the device as manufactured, they may be loaded into the process arrays after manufacture of the device, they may be loaded in the process arrays just before introduction of the sample, or they may be mixed with sample before loading into the process arrays.

A preferred method involves the use of a device with a plurality of process arrays such as those illustrated in U.S. patent application Ser. No. 09/894,810 filed on Jun. 28, 2001 and entitled ENHANCED SAMPLE PROCESSING DEVICES SYSTEMS AND METHODS (U.S. Pat. Application Publication No. 2002/0047003 A1 (Bedingham et al.)). Each of the process arrays includes a number of chambers (e.g., loading chambers and process chambers such as reaction chambers or clean-up chambers) that are preferably arranged generally radially on a device (such that centrifugal forces can move fluids sequentially from chamber to chamber, for example). The chambers within each of the arrays are in fluid communication using channels or other conduits that may, in some embodiments, include valve structures to control the movement as desired.

Using such a device, starting sample material, e.g., lysed blood cells, is provided in a loading chamber. A filter is preferably provided to filter the starting sample material as it moves from the loading chamber to a first process chambers. The first process chambers preferably include suitable PCR primers as supplied, e.g., dried down in each of the chambers. Each of the chambers may include the same primer or different primers depending on the nature of the investigation being performed on the starting sample material. One alternative to providing the primers in the process chambers before loading the sample is to add a suitable primer to the loading chamber with the starting sample material (provided that the primer is capable of passing through the filter, if present).

After locating the starting sample material and any required primers in the process chambers, the materials in the process chambers are thermally cycled under conditions suitable for PCR amplification of the selected genetic material.

After completion of the PCR amplification process, the materials in each of the first process chambers may be moved through another filter chamber (one filter chamber for each process chamber) to remove unwanted materials from the amplified materials, e.g., PCR primers, unwanted materials in the starting sample that were not removed by filter, etc. The filter chambers contain the active chemistry coated on surfaces of the chamber, for example. Alternatively, or additionally, they may contain the solid-phase materials described above for sample clean-up (e.g., dye removal). The area in which the active chemistry is included in such devices can be a chamber or in the volume defined by a connection between two chambers or both.

After clean-up of the sample materials in the filter chambers, the filtered PCR amplification products from each of the first process chambers are moved into second process chambers for, e.g., sequence cycling of the genetic materials amplified in the first process chambers through appropriate control of the thermal conditions encountered in second process chambers.

After completion of the sequence cycling (e.g., Sanger sequencing) process, the materials in each of the second process chambers may be moved through another filter chamber (one filter chamber for each process chamber) to remove unwanted materials from the sequencing ladders (e.g., sequencing primers, ddNTPs, etc.). The filter chambers contain the active chemistry coated on surfaces of the chamber, for example. Alternatively, or additionally, they may contain the solid-phase materials described above for sample clean-up (e.g., dye removal). Again, the active chemistry can be in a chamber or between chambers in a channel.

The present invention also provides devices for processing (e.g., clean-up) of sample mixtures. The sample materials may be located in a plurality of process chambers in the device which, in various aspects, may include one or more of: a reflective layer (e.g., a metallic layer); baffle structures to enhance cooling during rotation of the device; capture plugs to capture filtering materials; valve mechanisms capable of being selectively opened, thermal indicators for monitoring/controlling the temperatures in process chambers, absorptive materials in the process chambers to enhance energy absorption, etc. In various embodiments, the devices may include reagents, filters, and other sample processing materials in the process chambers.

Among the thermal control advantages of the devices of the present invention are chamber-to-chamber temperature uniformity, comparable chamber-to-chamber temperature transition rates, and the increased speed at which thermal energy can be added or removed from the process chambers. Among the device features than can contribute to these thermal control advantages are the inclusion of a reflective layer (e.g., metallic) in the device, baffle structures to assist in removing thermal energy from the device, and low thermal mass of the device. By including thermal indicators in the devices, enhanced control over chamber temperature may be achieved even as the device is rotated during processing.

One illustrative device manufactured according to the principles of the present invention is illustrated in FIG. 1. The device 10 is preferably in the shape of a circular disk as illustrated in FIG. 1, although any other shape that can be rotated could be used in place of the preferred circular disc. The device 10 of FIG. 1 is a multi-layered composite structure including a substrate first layer and a second layer.

The device includes a plurality of process chambers 50, each of which defines a volume for containing a sample and any other materials that are to be thermally cycled with the sample. The illustrated device 10 includes ninety-six process chambers 50, although it will be understood that the exact number of process chambers provided in connection with a device manufactured according to the present invention may be greater than or less than ninety-six, as desired.

The process chambers 50 in the illustrative device 10 are in the form of wells, although the process chambers in devices of the present invention may be provided in the form of capillaries, passageways, channels, grooves, or any other suitably defined volume. The process chambers 50 are in fluid communication with distribution channels 60 that, together with the common loading chamber 62, provide a distribution system for distributing samples to the process chambers 50. Introduction of samples into the device 10 through the loading chamber 62 may be accomplished by rotating the device 10 about a central axis of rotation such that the sample materials are moved outwardly due to centrifugal forces generated during rotation. Before the device 10 is rotated, the sample can be introduced into the loading chamber 62 for delivery to the process chambers 50 through distribution channels 60. The process chambers 50 and/or distribution channels 60 may include ports through which air can escape and/or features to assist in distribution of the sample materials to the process chambers 50. Alternatively, it may be possible to provide a closed distribution system, i.e., a system in which materials may be introduced through an opening through which air within the process chambers 50 and/or distribution channels 60 also escapes during the distribution process. In another alternative, sample materials could be loaded into the process chambers 50 under the assistance of vacuum or pressure.

The process chamber 50, associated distribution channels 60, and loading chamber 62 all combine to form a number of process arrays on the device 10, with each process array including one of the process chambers 50, the distribution channels 60 connecting the process chamber 50 to the loading chamber 62, and the loading chamber 62 itself. The process arrays may preferably be arranged radially on the device 10.

Figure 2:
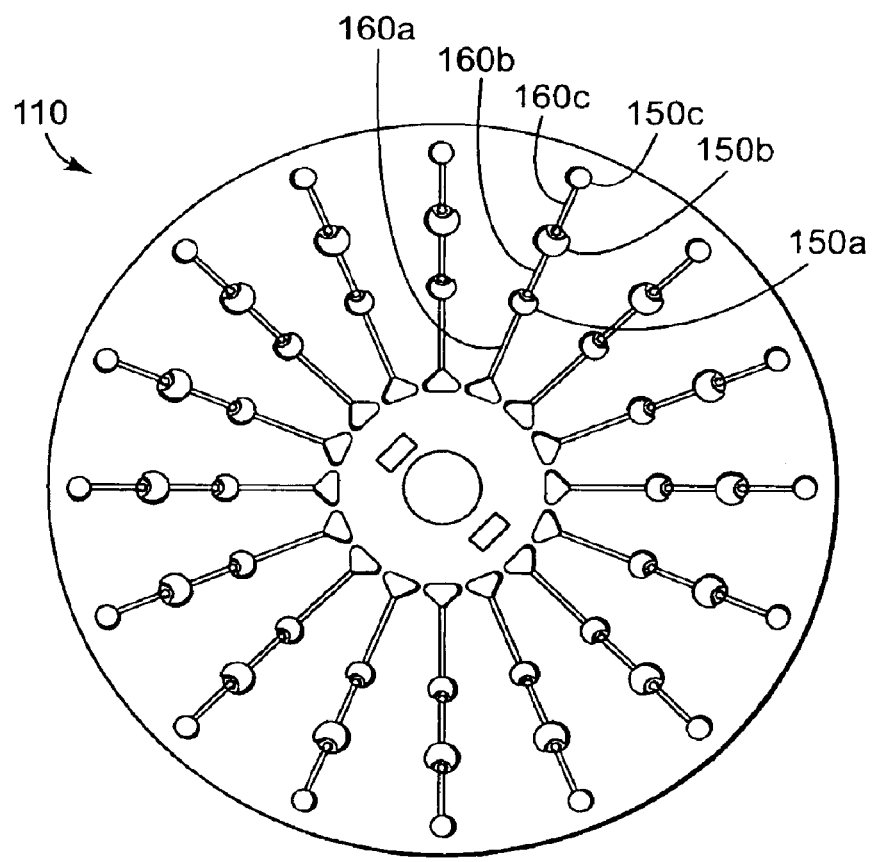
FIG. 2 depicts an alternative device that can be used in connection with the present invention.

Referring to FIGS. 2–4, an alternative device 110 with a different arrangement of process arrays is depicted that can be used in place of the device 10 of FIG. 1. The device 110 seen in FIG. 2 includes a number of independent process arrays, each of which includes distribution channels 160a and 160b connecting a loading chamber 162 and process chambers 150a, 150b and 150c. The process arrays on the device 110 are independent in the sense that the different process arrays are not in fluid communication with each other as are the process arrays on the device 10 of FIG. 1, but are, instead, separate and distinct from each other.

It is preferred that the process arrays be arranged radially from the center of the device 110. As a result, rotation of the device can be used to move sample materials successively through the chambers and distribution channels. The depicted device 110 includes sixteen process arrays, although it will be understood that devices used in connection with the present invention can include any desired number of process arrays. Furthermore, although each of the process arrays of device 110 includes a loading chamber and three process chambers connected sequentially by distribution channels, it should be understood that a process array of the present invention may include as few as two interconnected chambers.

FIG. 3 is an enlarged view of one process array on device 110 and FIG. 4 is a cross-sectional view of a portion of the process array of FIG. 3. Each process array includes a loading chamber 162 connected to a first process chamber 150a through a distribution channel 160a. The first process chamber 150a is, in turn, connected to a second process chamber 150b through a distribution channel 160b. The second process chamber 150b is connected to a third process chamber 150c, that, in the depicted process array, is located furthest from the loading chamber 162. If materials are to be moved within the process array from the loading chamber 162 towards the third process chamber 150c, it may be preferred that the loading chamber 162 be located closer to the axis of rotation of the device than the process chambers 150a, 150b or 150c.

The cross-sectional view of FIG. 4 depicts a number of other features of one potential construction of a device that could be used in connection with the present invention. The construction includes a core 180 in which the features of the device are formed. One surface 182 of the core 180 may include a cover film 184 attached thereto. The cover film 184 may be of any suitable construction, although the adhesive cover films described herein may be preferred.

The bottom of the process chamber 150a also includes a cover 186 attached to the surface 188 of the core 180 to enclose the volume of the process chamber 150a. Like the cover 184, it may be preferred that the cover 186 be attached to and seal with the core 180 using an adhesive, e.g. a pressure sensitive adhesive as described herein. It may be preferred that the cover 186 be provided in the form of a metallic layer that enhances thermal energy transfer into and out of the process chamber 150a. In some embodiments, the cover 186 may be provided in the form of a ring-shaped structure as described in, e.g., U.S. patent application Ser. No. 09/894,810 filed on Jun. 28, 2001 and entitled ENHANCED SAMPLE PROCESSING DEVICES, SYSTEMS AND METHODS (U.S. Pat. Application Publication No. 2002/0047003 A1 (Bedingham et al.)).

The first process chamber 150a includes a valve structure in the form of a lip 170a that protrudes into the boundaries of what would otherwise be a generally circular first process chamber 150a. The lip 170a is in the form of an undercut extension into the volume of the process chamber 150a as seen in, e.g., FIG. 4. When an opening is provided in the lip 170a, sample materials in the process chamber 150a can move into the distribution channel 160b for delivery to the second process chamber 150b is desired. In the absence of an opening in the lip 170a, movement of materials into the second process chamber 150b through distribution channel 160b is prevented by the lip 170a which otherwise seals against the cover 184 to prevent the flow of sample materials from the first process chamber 150a into the distribution channel 160b.

The lip 170a may preferably include an area 172a of reduced thickness. This may be seen best in the cross-sectional view of FIG. 4. When the area 172a is, e.g., pierced or otherwise deformed to include an opening formed therethrough, any sample materials located in the volume of the process chamber 150a can move from the chamber into the distribution channel 160b for delivery to the second process chamber 150b.

Although it is not required, the reduced thickness of the area 172a may provide a number of advantages. It may, for example, limit the location or locations in which the lip 170a may be easily pierced to provide the desired opening, i.e., the thicker portions of the lip 170a surrounding the area 172a may be more resistant to piercing by any of the techniques that could be used to pierce the lip 170a to form an opening therethrough. The techniques that could be used to pierce the lip 170a may include, e.g., mechanical piercing (using, e.g., a pin, needle, etc.), laser ablation, etc. Another potential advantage of the area 172a of reduced thickness is that it can be molded into the core layer 180 along with, e.g., the process chambers and distribution channels.

Although devices such as those described herein may be well-suited to performing processes such as e.g., PCR, Sanger sequencing, etc., devices of the invention may be limited to clean-up of the products of such processes which may be performed off of the devices.

Rotation of any device including process arrays such as those depicted in FIGS. 1–4 may be used to facilitate mixing through mechanical agitation of the sample materials and any other materials (e.g., reagents, etc.) present in the process chambers. The mechanical agitation may be accomplished by oscillating the device in opposite directions about the axis of rotation. The oscillations may vary in frequency and/or magnitude depending on a variety of factors, e.g., the size/shape of the process chambers, the amount of materials in the process chambers, viscosities, temperatures, stability of the sample materials, etc. For example, it may be useful to accomplish mixing by oscillating the device 10 at a frequency of about 1 Hertz (Hz) to about 100 Hertz. The magnitude of the oscillations may be, e.g., from about 5 degrees to about 360 degrees.

The mechanical agitation can be carried out during, for example, PCR, Sanger cycling, clean-up of the PCR reaction mixture, clean-up of the sequencing reaction mixture, as well as during various other processes that can be carried out in the microfluidic devices described herein. Similarly, mechanical agitation by rotation, or other means, can be carried out on any of the devices described herein.

EXAMPLES

Objects and advantages of this invention are further illustrated by the following examples, but the particular materials and amounts thereof recited in these examples, as well as other conditions and details, should not be construed to unduly limit this invention.

Example 1

Preparation of PES/PSSA Membrane Columns for Sequencing Reaction Clean-up

A 47-millimeter (47-mm) diameter disk of polyethersulfone (PES)/copolymer ion-exchange membrane available under the trade designation SB-6407 from Pall Corp., East Hills, N.Y. was dipped briefly in methanol to thoroughly wet the membrane and then washed with distilled water before transferring to a poly(sodium 4-styrenesulfonate) (PSSA) solution in deionized water. The PES membrane contains quaternary ammonium groups grafted onto the surface of the membrane. The PES membrane was soaked overnight in various weight percents of PSSA solutions (challenge concentrations) as indicated below, then washed 4 times with distilled water, and allowed to air dry.

The PES membrane with PSSA challenge concentrations of 0.01 wt-% to 0.1 wt-% were prepared as described above. Disks (4 mm diameter) of PSSA-coated PES membrane were placed in a 4-mm diameter column fitted with a polyethylene Porex frit (50–100µ pore size; obtained from Porex Corporation, Fairburn, Ga.) and a retaining ring (4 mm diameter) was placed on top of the membrane to hold the membrane in place. Ten microliters (10 µL) quarter strength BIGDYE Terminators v 2.0 (Applied Biosystems, Inc., Foster City, Calif.) cycle sequencing reaction mixtures containing 2 µL BIGDYE mix, 200 nanogram (ng) DNA template, and 1.6 picomoles of a primer were thermocycled according to manufacturers instructions in a GENEAMP PCR System 9700 thermocycler (Applied Biosystems Inc.). Five to ten microliters (5 to 10 µL) of the unpurified sequencing reaction mixture (containing dye terminators and their hydrolysis products, DNA template, Taq polymerase, buffer, dNTPs, and primers) were pipetted onto each column and samples were centrifuged for 2 minutes at 750×g to collect eluent. Ten to fifteen microliters (10 to 15 µL) of sterile water were added to each sample and analyzed by Capillary electrophoresis (CE) and reverse phase high pressure liquid chromatography (HPLC) to assess sample quality.

Example 2

Screening of PES/PSSA Membranes for Clean-up of BIGDYE Terminators v 2.0 Sequencing Reactions Using Capillary Electrophoresis and Reverse Phase HPLC Capillary electrophoresis (CE) and reverse phase HPLC were used as analytical tools to evaluate the performance of materials for clean-up of sequencing reaction mixtures, specifically removal of dye terminators and sequencing ladder recovery, prior to sequencing analysis by ABI PRISM 310 or 3100 Genetic Analyzer (Applied Biosystems, Inc.).

Capillary Electrophoresis: Capillary electrophoresis analysis of purified sequencing reactions (purified as described in Example 1) was done with Beckman P/ACE MDQ Capillary Electrophoresis instrument (Beckman Coulter, Fullerton, Calif.) with a fluorescence detector (488-nanometer (nm) excitation, 530 nm to 700 nm emission) using a 75 micrometer ID, 30 cm long (20 cm to the detector) fused silica capillary. Runs were performed at 500 volts per centimeter (V/cm) (15 KV total) using 50 millimolar (mM) Tris-HCl/1 mM EDTA (pH 8.5) as the running buffer. Sample injection was done at 690 pascals for 5 seconds. The conditions used gave good separation of the dye terminators (all the four ddNTPs corresponding to the four bases, A, T, G, C as one peak with a retention time of 3.2 minutes) and its degradation products (as one peak with a retention time of 2.2 minutes) and the combined sequencing ladder (as one peak with a retention time of 4.1 minutes). Sequencing ladder and dye terminator concentrations were obtained by integrating the peak area of the various analytes. For each of the samples, the baseline was subtracted from the analyte values and the resulting analyte concentration was represented as a percentage of the starting sequencing reaction. CE results showed that the dye terminators and its degradation products content was brought down to less than 2% of the original concentration and the DNA content in solution was at least 30% of the starting concentration. This trend held for PSSA challenge concentrations ranging from 0.01 wt-% through 0.11 wt-% (Table 1). These data revealed that the dye terminator removal and sequencing ladder recovery was dependent on PSSA passivation level. For particularly good sequencing data, the samples fulfilled the following two conditions: 1) dye terminator removal was greater than 98%; and 2) recovery of sequencing ladder was at least 30%.

TABLE 1

| Percent PSSA Challenge Concentration | Percent Sequencing Ladder Recovery | Percent BIGDYE Recovery |
|---|---|---|
| 0 | 0 | 0 |
| 0.01 | 44 | <2% |
| 0.02 | 45 | <2% |
| 0.04 | 65 | <2% |
| 0.05 | 60 | <2% |
| 0.06 | 90 | <2% |
| 0.10 | 100 | 10% |

Reverse Phase HPLC: HPLC analysis of purified sequencing reactions (purified as described in Example 1) was performed on a Waters ALLIANCE 2690 separations module with a 474 scanning fluorescence detector and a 996 photodiode array detector and a C18 column (Waters Corporation, Milford, Mass.). The mobile phase used was 70% triethylamine acetate (TEAaC) and 30% acetonitrile with a flow rate of 0.1 milliliter per minute (mL/min). A 2.5-µL sample of purified sequencing reaction was injected and the run time was for 15 minutes. Analysis was done using the fluorescence detector and the conditions used gave good separation of the dye terminators (all the four ddNTPs corresponding to the four bases, A, T, G, C as one peak) and their degradation products (as one peak). The dye terminator concentrations were obtained by integrating the peak area of the various analytes. For each of the samples, the baseline was subtracted from the analyte values and the resulting analyte concentration was represented as a percentage of the starting sequencing reaction. Again, the data obtained revealed that the dye terminator removal was dependent on PSSA passivation level. For particularly good sequencing data, dye terminator removal was greater than 98%. These results correlated well with the results obtained using capillary electrophoresis.

Example 3

BIGDYE Terminators v 2.0 Sequencing Reaction Clean-Up with PES/PSSA Membrane Columns Various PES/PSSA membrane columns were prepared as described in Example 1. Five to ten microliters (5 to 10 µL) of an unpurified quarter strength sequencing reaction mixture (containing dye terminators and their hydrolysis products, DNA template, Taq polymerase, buffer, dNTPs, and primer) were pipetted onto each column and samples were purified as described in Example 1. The purified sequencing reactions were analyzed using rapid sequencing module on an ABI PRISM 310 Genetic Analyzer (Applied Biosystems, Inc.). The resulting electropherograms were manually checked for quality (like dye blobs, number of Ns) and compared against the reference sequence using the BLAST program available through GenBank. In addition, the electropherograms were analyzed using Phred base calling program (Codoncode Corp., Dedham, Mass.). The Phred program generates highly accurate, base-specific quality scores. The quality scores are an ideal tool to assess the quality of sequences. The Phred quality scores generated for the sequencing reactions purified using PES/PSSA membrane columns are shown below in Table 2. The results indicated that the PES/PSSA membranes gave good sequencing data that was comparable to data generated using CENTRISEP columns (Princeton Separations, Adelphia, N.J.), which is considered an industry standard. Average read length of successful reactions was 400 bases with 97% to 98% base-calling accuracy.

TABLE 2

| Sample | Scores ≥20 | Scores ≥30 | Scores ≥40 | Classification |
|---|---|---|---|---|
| 0.01% PSSA | 150 | 32 | 6 | Bad |
| 0.015% PSSA | 148 | 54 | 22 | Bad |
| 0.02% PSSA | 266 | 126 | 54 | Good |
| 0.025% PSSA | 293 | 186 | 40 | Good |
| 0.03% PSSA | 373 | 272 | 131 | Good |
| 0.035% PSSA | 232 | 104 | 39 | Good |
| 0.04% PSSA | 315 | 192 | 79 | Good |
| 0.045% PSSA | 277 | 160 | 58 | Good |
| 0.05% PSSA | 281 | 164 | 62 | Good |
| 0.055% PSSA | 290 | 165 | 50 | Good |
| 0.06% PSSA | 264 | 151 | 61 | Good |
| 0.065% PSSA | 295 | 180 | 85 | Good |
| 0.07% PSSA | 279 | 168 | 49 | Good |
| 0.075% PSSA | 202 | 81 | 15 | Good |
| CENTRISEP | 290 | 182 | 66 | Good |

Example 4

BIGDYE Terminators v 2.0 Sequencing Reaction Clean-Up Using Microfluidic Disk and PES/PSSA Membrane A simplified microfluidic disk was used that consisted of eight duplicate processing lanes arranged radially in a laminated polypropylene disk (80 mm diameter, 0.030-inch thick (762 µm thick). Each processing lane consisted of a single combined input and clean-up chamber (circular well, 7.11 mm diameter, located on a 16.5 mm radius) that is connected to an output chamber (circular well, 4-mm diameter, located on a 29.0 mm radius) by a single channel (0.010-inch deep (254 µm deep), 0.015-inch wide (381 µm wide).

Clean up was accomplished using PES/PSSA membranes prepared as described in Example 1. For optimal levels of passivation, PSSA challenge concentrations from 0.001 wt-% to 0.1 wt-% PSSA were used. Disks (3.2 mm diameter) of the membrane were positioned onto an adhesive cover film (9795R Advanced Sealing Tape, 3M Medical Specialties, St. Paul, Minn.) which was laminated onto a microfluidic disk with the membrane registered such that it covered the top and/or bottom of clean-up chambers. Five microliters (5 µL) of an unpurified quarter strength BIGDYE Terminators v 2.0 sequencing reaction mixture containing 2 µL BIGDYE mix, 200 ng DNA template, and 1.6 picomoles of a primer were introduced into the clean-up chamber and allowed to sit for up to 20 minutes. Mixing the solution while in contact with the membrane reduced the time needed to carry out the clean-up. Over this time, the smaller molecules in the unpurified sequencing solution (containing dye terminators and their hydrolysis products, DNA template, Taq polymerase, buffer, dNTPs, and primers) were bound to the membrane and the sequencing ladder was left in solution. Removal of the solution from the clean-up chamber followed by dilution to 10–15 µL in sterile water yielded a sample that was ready for sequencing.

The samples were analyzed by ABI PRISM 3100 Genetic Analyzer under standard sequencing conditions (Applied Biosystems, Inc.). The resulting electropherograms were manually checked for quality and base calling accuracy using BLAST and Phred program as described in Example 3. The Phred quality scores generated for sequencing reactions purified using PES/PSSA membranes in a microfluidic disk are shown below in Table 3. The results indicated that the PES/PSSA membranes gave good sequencing data that was comparable to data generated using CENTRISEP columns. Average read length of successful reactions was 600 bases with 97% to 98% base-calling accuracy.

TABLE 3

| Sample | Scores ≧20 | Scores ≧30 | Scores ≧40 | Classification |
|---|---|---|---|---|
| 0% PSSA | 45 | 3 | 0 | Bad |
| 0.001% PSSA | 491 | 377 | 272 | Good |
| 0.003% PSSA | 553 | 449 | 352 | Good |
| 0.005% PSSA | 451 | 297 | 153 | Good |
| 0.010% PSSA | 457 | 336 | 231 | Good |
| 0.0125% PSSA | 541 | 427 | 327 | Good |
| 0.020% PSSA | 502 | 429 | 316 | Good |
| CENTRISEP | 550 | 480 | 350 | Good |

Example 5

BIGDYE Terminators v 2.0 Sequencing Reaction Clean-Up with Polyquat/PSSA Coated Adhesive A layer containing quaternary ammonium ion groups was prepared by combining 2.75 grams (g) of gelatin (75 bloom from Bovine Serum, Sigma, St. Louise, Mo.) with 19 mL of deionized water and heating at 60–70° C. until dissolved. A polyquat solution (3.5 mL) of a copolymer of trimethyl aminoethyl methacrylate and methyl methacrylate in a 60:40 ratio of propylene glycol methyl ether:water (available under the trade designation SYNTRAN Hx31-65 from Interpolymer Corp., Canton, Mass.) was added along with 4–5 drops of a heat-activated chemical crosslinker (an aliphatic triglycidyl ether) commercially available under the trade designation HELOXY Modifier 48 from Resolution Performance Products, Houston, Tex. A sample of an oxygen plasma treated pressure sensitive silicone adhesive (9795R Advanced Sealing Tape, 3M Medical Specialties, St. Paul, Minn.) was dipped into this solution and heated at 115–120° C. for 15 minutes to remove the solvent, then thoroughly washed with deionized water to form a 13-µm thick film. The coated adhesives were then soaked overnight in 0.001 wt-% to 0.06 wt-% solutions of PSSA, washed again in water, and air-dried.

The polyquat/PSSA coated adhesive described above was applied to the top and/or bottom of clean-up chambers of a microfluidic disk (FIG. 2) as described in Example 4. In this example, 5 µL sequencing reaction mixtures (containing 1 µL BIGDYE v 2.0 mix, 200 ng template, and 1.6 picomoles of a primer) were cycled in a processing chamber of the device, a valve was opened, the unpurified reaction mixture entered the processing chamber for clean-up, the device was mechanically agitated by shaking the disk at a frequency of 12–14 Hz with an angular displacement of 20 degrees for a short time (under 10 minutes), and then a second valve was opened to allow the purified reaction mixture out. The purified reactions were removed and analyzed by ABI PRISM 3100 Genetic Analyzer under standard sequencing conditions (Applied Biosystems, Inc.).

The resulting electropherograms were manually checked for quality and base-calling accuracy using BLAST and Phred program as described in Example 3. The Phred quality scores generated for sequencing reactions purified using polyquat/PSSA coated adhesive in a microfluidic disk are shown below in Table 4. The results indicated that the polyquat/PSSA coated adhesive gave good sequencing data that was comparable to data generated using CENTRISEP columns. Average read length of successful reactions was 650 bases with 97% to 98% base-calling accuracy.

TABLE 4

| Sample | Scores ≧20 | Scores ≧30 | Scores ≧40 | Classification |
|---|---|---|---|---|
| 0.001% PSSA | 521 | 407 | 300 | Good |
| 0.005% PSSA | 568 | 453 | 352 | Good |
| 0.01% PSSA | 606 | 498 | 370 | Good |
| 0.02% PSSA | 627 | 528 | 400 | Good |
| 0.06% PSSA | 598 | 474 | 367 | Good |
| CENTRISEP | 599 | 487 | 395 | Good |

Example 6

BIGDYE Terminators v 2.0 Sequencing Reaction Clean-Up with Polyquat/PSSA Coated Polycarbonate Method 1. A layer containing quaternary ammonium ion groups was prepared by combining 2.75 grams (g) of gelatin (75 bloom from Bovine Serum, Sigma, St. Louise, Mo.) with 19 mL of deionized water and heating at 60–70° C. until dissolved. A polyquat solution (3.5 mL) of a copolymer of trimethyl aminoethyl methacrylate and methyl methacrylate in a 60:40 ratio of propylene glycol methyl ether:water (available under the trade designation SYNTRAN Hx31-65 from Interpolymer Corp., Canton, Mass.) was added along with 4–5 drops of the HELOXY Modifier 48 crosslinker commercially available from Resolution Performance Products, Houston, Tex. A sample of an oxygen plasma treated polycarbonate was wire-coated with 300-mm gap and heated at 115–120° C. for 15 minutes to remove the solvent, then thoroughly washed with deionized water to form a 2.6-µm thick film. The coated adhesives were then soaked overnight in 0.0001 wt-% to 0.1 wt-% solutions of PSSA, washed again in water, and air-dried.

Method 2. A polyquat solution (3 mL) of a copolymer of trimethyl aminoethyl methacrylate and methyl methacrylate in a 60:40 ratio of propylene glycol methyl ether:water (available under the trade designation SYNTRAN Hx31-65 from Interpolymer Corp., Canton, Mass.) was added to 3 mL of diethylene glycol butyl ether, 20 µL of dibutyl phthalate (plasticizer) along with 3 drops of the HELOXY Modifier 48 crosslinker commercially available from Resolution Performance Products, Houston, Tex. A sample of an oxygen plasma treated polycarbonate was wire-coated with a 300-mm gap, air-dried overnight and heated at 115–120° C. for 15 minutes to remove the solvent, then thoroughly washed with deionized water to form a 2.6-µm thick dry film. The coated adhesives were then soaked overnight in a 0.0001 wt-% to 0.1 wt-% solutions of PSSA, washed again in water, and air-dried.

The polyquat/PSSA coated polycarbonate was applied to the top and/or bottom of clean-up chambers of a microfluidic disk (FIG. 2) as described in Example 4. Five microliters (5 μL) of unpurified BIGDYE v 2.0 quarter strength sequencing reaction was introduced into the clean-up chambers and purified as described in Example 5. The purified samples were removed from the microfluidic disk and analyzed by ABI PRISM 3100 Genetic Analyzer under standard sequencing conditions (Applied Biosystems, Inc.).

The resulting electropherograms were manually checked for quality and base-calling accuracy using BLAST and Phred program as described in Example 3. The Phred quality scores generated for the sequencing reactions purified using polyquat/PSSA coated polycarbonate in a microfluidic disk are shown below in Table 5. The results indicated that the polyquat/PSSA coated polycarbonate gave good sequencing data that was comparable to data generated using CENTRISEP columns. Average read length of successful reactions was 600 to 650 bases with 97% to 98% base-calling accuracy.

TABLE 5

| Sample | Scores ≧20 | Scores ≧30 | Scores ≧40 | Classification |
|---|---|---|---|---|
| 0.0001% PSSA Method 1 | 585 | 469 | 359 | Good |
| 0.0005% PSSA Method 1 | 590 | 458 | 363 | Good |
| 0.001% PSSA Method 1 | 590 | 470 | 373 | Good |
| 0.0005% PSSA Method 2 | 557 | 423 | 325 | Good |
| 0.001% PSSA Method 2 | 539 | 434 | 318 | Good |
| 0.005% PSSA Method 2 | 551 | 437 | 316 | Good |
| CENTRISEP | 630 | 466 | 349 | Good |

Example 7

BIGDYE Terminators v 3.0 Sequencing Reaction Clean-Up with PES/PSSA Membrane Columns Spin columns with 4-mm disks of PES/PSSA membrane were prepared as described in Example 1. Ten microliters (10 μL) quarter strength BIGDYE Terminators v 3.0 (Applied Biosystems, Inc.) cycle sequencing reaction mixtures containing 2 μL BIGDYE mix, 200 ng DNA template and 1.6 picomoles of a primer were thermocycled according to manufacturers instructions in a GENEAMP PCR System 9700 thermocycler (Applied Biosystems Inc). Five to ten microliters (5 to 10 μL) of the unpurified quarter strength sequencing reaction mixture (containing dye terminators and their hydrolysis products, DNA template, Taq polymerase, buffer, dNTPs, and primer) were pipetted onto each column and samples were purified as described in Example 1. The samples were diluted to 10 μL and analyzed by ABI PRISM 310 Genetic Analyzer using rapid sequencing module (Applied Biosystems, Inc.). The resulting electropherograms were manually checked for quality and base calling accuracy using BLAST and Phred program as described in example 3. The Phred quality scores generated for the BIGDYE v 3.0 sequencing reactions purified with PES/PSSA membranes are shown below in Table 6. The results indicated that the PES/PSSA membranes gave good sequencing data that was comparable to data generated using CENTRISEP columns. Average read length of successful reactions was 400 bases with 97% to 98% base-calling accuracy.

TABLE 6

| Sample | Scores ≧20 | Scores ≧30 | Scores ≧40 | Classification |
|---|---|---|---|---|
| CENTRISEP | 277 | 117 | 36 | Good |
| 0.005% PSSA | 2 | 0 | 0 | Bad |
| 0.01% PSSA | 11 | 0 | 0 | Bad |
| 0.015% PSSA | 61 | 7 | 1 | Bad |
| 0.02% PSSA | 239 | 84 | 34 | Good |
| 0.025% PSSA | 229 | 107 | 48 | Good |
| 0.03% PSSA | 259 | 136 | 52 | Good |
| 0.035% PSSA | 229 | 107 | 48 | Good |
| 0.04% PSSA | 257 | 124 | 59 | Good |
| 0.045% PSSA | 238 | 114 | 56 | Good |
| 0.055% PSSA | 154 | 40 | 8 | Bad |
| 0.075% PSSA | 22 | 3 | 3 | Bad |

Example 8

DYEnamic ET Dye Terminators Sequencing Reaction Clean-Up with PES/PSSA Membrane Columns Spin columns with 4-mm disks of PES/PSSA membrane and a retaining ring of 1.0 mm or 4 mm were prepared as described in Example 1. Ten microliters (10 μL) quarter strength DYEnamic ET Dye terminators (Amersham Biosciences, Piscataway, N.J.) cycle sequencing reaction mixtures containing 2 μL DYEnamic ET Dye terminators mix, 200 ng DNA template, and 1.6 picomoles of a primer were thermocycled according to manufacturers instructions in a GENEAMP PCR System 9700 thermocycler (Applied Biosystems Inc.). Five to ten microliters (5 to 10 μL) of the unpurified quarter strength sequencing reaction mixture (containing dye terminators and their hydrolysis products, DNA template, Taq polymerase, buffer, dNTPs, and primer) were pipetted onto each column and samples were purified as described in Example 1. The samples were diluted to 10 μL and analyzed by ABI PRISM 3100 Genetic Analyzer under standard sequencing conditions (Applied Biosystems, Inc.). The resulting electropherograms were manually checked for quality and base-calling accuracy using BLAST and Phred program as described in Example 3. The Phred quality scores generated for DYEnamic ET Dye terminators sequencing reactions purified with PES/PSSA membranes are shown below in Table 7. The results indicated that the PES/PSSA membranes gave good sequence data that was comparable to data generated using CENTRISEP columns. Average read length of successful reactions was 600 bases with 97% to 98% base-calling accuracy.

TABLE 7

| Sample | Scores ≧20 | Scores ≧30 | Scores ≧40 | Classification |
|---|---|---|---|---|
| 0.005% PSSA (1 mm) | 0 | 0 | 0 | Bad |
| 0.005% PSSA (4 mm) | 0 | 0 | 0 | Bad |
| 0.025% PSSA (1 mm) | 439 | 288 | 152 | Good |
| 0.025% PSSA (4 mm) | 356 | 213 | 111 | Good |
| 0.03% PSSA (1 mm) | 423 | 329 | 200 | Good |
| 0.03% PSSA (4 mm) | 328 | 187 | 103 | Good |
| 0.035% PSSA (1 mm) | 440 | 325 | 195 | Good |
| 0.035% PSSA (4 mm) | 245 | 149 | 63 | Good |
| 0.04% PSSA (1 mm) | 462 | 353 | 219 | Good |
| 0.04% PSSA (4 mm) | 403 | 263 | 162 | Good |
| 0.045% PSSA (1 mm) | 449 | 330 | 192 | Good |
| 0.045% PSSA (4 mm) | 391 | 287 | 174 | Good |
| 0.05% PSSA (1 mm) | 404 | 315 | 193 | Good |
| 0.05% PSSA (4 mm) | 437 | 285 | 150 | Good |

TABLE 7-continued

| Sample | Scores ≧20 | Scores ≧30 | Scores ≧40 | Classification |
|---|---|---|---|---|
| 0.07% PSSA (4 mm) | 330 | 210 | 89 | Good |
| 0.08% PSSA (4 mm) | 324 | 193 | 82 | Good |
| 0.1% PSSA (4 mm) | 381 | 215 | 82 | Good |
| CENTRISEP | 556 | 419 | 275 | Good |

Example 9

BIGDYE Terminators v 2.0 Sequencing Reaction Clean-Up with PES/PSSA Membrane in a 96-well Plate Format A 96-well filtration plate of the type described in U.S. Pat. No. 5,620,663 (Aysta et al.) modified by replacing the filter material with PES membranes challenged with various concentration of PSSA was constructed as follows. Disks (8 mm diameter) of PES/PSSA membrane (prepared as described in example 1) were placed in the wells of the plate fitted with a spunbond polypropylene nonwoven material with a basis weight of 67 gms/m$^2$ (CELESTRA, BBA Filtration, Simpsonville, S.C.) and a retaining ring (4 mm or 1.5 mm diameter) described in U.S. Pat. No. 5,620,663 (Aysta et al.) to hold the membrane in place on top the nonwoven material.

A 10 μL BIGDYE v 2.0 quarter strength sequencing reaction mixture was added to the wells of the 96-well PES/PSSA membrane plate described above and spun at 500×g for 2 minutes in a plate centrifuge. The eluent was collected into a collection plate and analyzed by ABI PRISM 3100 Genetic Analyzer under standard sequencing conditions (Applied Biosystems, Inc.). The resulting electropherograms were manually checked for quality and base-calling accuracy using BLAST and Phred program as described in Example 3. The Phred quality scores generated for BIGDYE v 2.0 sequencing reaction mixtures purified with a 96-well PES/PSSA membrane plate are shown below in Table 8. The results indicated that the 96-well PES/PSSA membrane plate gave good sequencing data that was comparable to data generated using CENTRISEP columns. Average read length of successful reactions was 650 bases with 97% to 98% base-calling accuracy.

TABLE 8

| Sample | Scores ≧20 | Scores ≧30 | Scores ≧40 | Classification |
|---|---|---|---|---|
| 0.005% PSSA 1.5 mm | 0 | 0 | 0 | Bad |
| 0.005% PSSA 4 mm | 0 | 0 | 0 | Bad |
| 0.01% PSSA 1.5 mm | 0 | 0 | 0 | Bad |
| 0.01% PSSA 4 mm | 0 | 0 | 0 | Bad |
| 0.02% PSSA 1.5 mm | 563 | 453 | 299 | Good |
| 0.02% PSSA 4 mm | 311 | 104 | 27 | Good |
| 0.03% PSSA 1.5 mm | 479 | 342 | 154 | Good |
| 0.03% PSSA 4 mm | 495 | 322 | 148 | Good |
| 0.04% PSSA 1.5 mm | 548 | 426 | 246 | Good |
| 0.04% PSSA 4 mm | 560 | 430 | 248 | Good |
| 0.05% PSSA 1.5 mm | 467 | 319 | 157 | Good |
| 0.05% PSSA 4 mm | 530 | 295 | 160 | Good |
| 0.06% PSSA 1.5 mm | 225 | 88 | 20 | Good |
| 0.06% PSSA 4 mm | 202 | 73 | 11 | Good |
| 0.07% PSSA 1.5 mm | 416 | 250 | 84 | Good |
| 0.07% PSSA 4 mm | 262 | 125 | 38 | Good |
| 0.08% PSSA 1.5 mm | 107 | 9 | 1 | Bad |

TABLE 8-continued

| Sample | Scores ≧20 | Scores ≧30 | Scores ≧40 | Classification |
|---|---|---|---|---|
| 0.08% PSSA 4 mm | 127 | 23 | 9 | Bad |
| CENTRISEP | 626 | 511 | 421 | Good |

Example 10

Polymerase Chain Reaction (PCR) Clean-Up Using PES/PSSA Membrane

Briefly, a typical PCR reaction contains 200 nM of each of the two primers and 200 μM of each of the four dNTPs (dGTP, dATP, dCTP and dTTP). Most of the residual primers and dNTPs after a thermocycling reaction need to be removed as the residual dNTPs and primers can interfere in subsequent down-stream applications such as sequencing reaction. At the same time sufficient amount of PCR product needs to be recovered for further processing. The ability of PES/PSSA membranes to remove primers and dNTPs and recover PCR amplicons and clean-up a PCR reaction for further processing was analyzed.

Primer Removal: Various PES/PSSA membrane columns were prepared as described in Example 1. A known amount (1 to 10 picomoles) of an oligonucleotide (M13/PUC sequencing primer (−47) (24-mer), New England Biolabs, Beverly, Mass.) in 10 μL 1×PCR buffer (Applied Biosystems, Inc.) was added to the column and spun at 750×g for 2 minutes to collect eluent. The amount of primers remaining in the eluent was determined using the OLI-GREEN ssDNA quantitation reagent (Molecular Probes, Eugene, Oreg.). The amount of primer left over in solution (i.e., not bound to the clean-up media) is shown below in Table 9. This was dependent on the PSSA challenge concentration level. The PES membrane challenged with 0.075% PSSA concentration was able to bind about 100% of the primer when challenged with 1 picomole, while it bound about 80% when challenged with 10 picomoles of the primer.

TABLE 9

| Challenge PSSA Concentration (%) | 1 Picomole Primer | 10 Picomole Primer |
|---|---|---|
| 0 | 0 | 0 |
| 0.015 | 0 | 0.10 |
| 0.075 | 0.02 | 2.2 |
| 0.20 | 0.02 | 5.0 | dNTP removal: Various PES/PSSA membrane columns were prepared as described in Example 1. A known amount of dNTPs (8 nanomoles with equal amounts of each of the four dNTPs) in 10 μL 1×PCR buffer (Applied Biosystems, Inc.) was added to the column and spun at 750×g for 2 minutes (min) to collect eluent. The amount of dNTPs remaining in the eluent was determined using absorbance at 260 nm in a spectrophotometer. The amount of dNTPs left over in solution (i.e., not bound to the clean up media) is shown below in Table 10. This was also dependent on the PSSA challenge concentration level. The PES membrane challenged with 0.075% PSSA concentration was able to bind about 80% of the dNTPs.

TABLE 10

| Challenge PSSA Concentration (%) | Nanomoles of dNTP Left in Solution |
|---|---|
| 0 | 0.43 |
| 0.015 | 1.2 |
| 0.075 | 2.0 |
| 0.20 | 5.4 |

PCR product recovery: Various PES/PSSA membrane columns were prepared as described in Example 1. A known amount of PCR amplicon (35 ng) ranging in size from 150 to 930 base pairs (bp) in 10 µL 1×PCR buffer (Applied Biosystems, Inc.) was added to the column and spun at 750×g for 2 minutes to collect eluent. The amount of PCR amplicon remaining in the eluent was determined by Agilent 2100 Bioanalyzer using a DNA 7500 lab chip kit (Agilent Technologies). The amount of PCR amplicons left over in solution and percent recovery (i.e., not bound to the clean up media) is shown below in Table 11. This was dependent on the PSSA challenge concentration level and size of the PCR amplicon. The recovery of PCR product from PES membrane challenged with 0.075% PSSA concentration ranged from 50% to 80% depending on the size of the PCR amplicon.

TABLE 11

| Amplicon size | 0% PSSA | 0.015% PSSA | 0.075% PSSA | 0.2% PSSA |
|---|---|---|---|---|
| 150 bp | 0 | 7.1 (20%) | 17 (49%) | 22 (63%) |
| 330 bp | 0 | 9.3 (27%) | 20 (57%) | 30 (86%) |
| 550 bp | 0 | 19 (54%) | 25 (71%) | 30 (86%) |
| 930 bp | 0 | 21 (60%) | 28 (80%) | 32 (91%) |

PCR product purification in a microfluidic disk: A microfluidic disk (FIG. 2) with reaction and clean-up chambers containing PES/PSSA membrane (challenged with 0.075% PSSA concentration) was constructed as described in Example 4. In this example, 5 µL PCR cocktail (containing 1×PCR buffer, 200 nM of each of the two primers, 200 µM of each of the four dNTPs, 1 ng DNA template, and 0.125 units of AmpliTaq DNA polymerase (Applied Biosystems, Inc.)) were cycled in a processing chamber of the device, a valve was opened, the unpurified reaction mixture entered the processing chamber for clean-up, the device was mechanically agitated by shaking the disk at a frequency of 12–14 Hz with an angular displacement of 20 degrees for a short time (under 10 minutes), and then a second valve was opened to allow the purified reaction mixture out. The purified PCR amplicons were used for sequencing and the sequencing reactions were purified with PES/PSSA membrane (challenged with 0.02% PSSA) columns as described in Example 1 and analyzed by ABI PRISM 3100 Genetic Analyzer under standard sequencing conditions (Applied Biosystems, Inc.). The resulting electropherograms were evaluated as described in Example 3. The electropherograms gave good sequencing data and yielded Phred scores of ≧20 for 500 to 600 bases (for larger amplicons).

Patents, patent applications, and publications disclosed herein are hereby incorporated by reference (in their entirety) as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A method of removing small negatively charged organic molecules from a biological sample mixture, the method comprising:
    providing a device comprising a plurality of process arrays, wherein each process array of the plurality of process arrays comprises:
        a plurality of process chambers, each of the process chambers defining a volume for containing a biological sample mixture; and
        at least one distribution channel connecting the plurality of process chambers of the array; wherein at least one of the process arrays comprises a surface comprising an anion exchange material partially coated with a negatively charged polymer;
    providing a biological sample mixture comprising small negatively charged organic molecules having a molecular weight of less than about 6,000; wherein the biological sample mixture is selected from the group consisting of a nucleic acid amplification reaction mixture and a nucleic acid labeling reaction mixture; and
    contacting the biological sample mixture with the surface comprising the anion exchange mnaterial to remove at least a portion of the small negatively charged organic molecules from the biological sample mixture.

2. A method of removing small negatively charged organic molecules from a biological sample mixture, the method comprising:
    providing a device comprising a plurality of process arrays, wherein each process array of the plurality of process arrays comprises:
        a plurality of process chambers, each of the process chambers defining a volume for containing a biological sample mixture; and
        at least one distribution channel connecting the plurality of process chambers of the array; wherein at least one of the process arrays comprises a surface comprising an anion exchange material partially coated with a negatively charged polymer;
    providing a biological sample mixture; and
    contacting the biological sample mixture with the surface comprising an anion exchange material partially coated with a negatively charged polymer to remove at least a portion of the small negatively charged organic molecules from the biological sample mixture.

3. The method of claim 2 wherein the negatively charged polymer is a polyelectrolyte.

4. The method of claim 3 wherein the negatively charged polyelectrolyte is selected from the group consisting of a polystryene sulfonic acid, polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, salts thereof, and mixtures thereof.

5. The method of claim 2 wherein the anion exchange material comprises quaternized nitrogen.

6. The method of claim 2 wherein the biological sample mixture is a nucleic acid sequencing reaction mixture.

7. The method of claim 6 wherein the small negatively charged organic molecules are selected from the group consisting of dye-labeled terminators, primers, degraded dye molecules, deoxynucleotide triphosphates, and mixtures thereof.

8. The method of claim 7 wherein the small negatively charged organic molecules comprise dye-labeled terminators.

9. The method of claim 8 wherein the dye-labeled terminators are selected from the group consisting of dideoxynucleotide triphosphates, dideoxynucleotide diphosphates, dideoxynucleotide monophosphates, dideoxynucleosides, and combinations thereof.

10. The method of claim 8 wherein contacting the biological sample mixture with the surface comprising an anion exchange material partially coated with a negatively charged polymer is carried out under conditions effective to remove substantially all the dye-labeled terminators from the biological sample mixture.

11. The method of claim 2 wherein the biological sample mixture is a PCR reaction mixture.

12. The method of claim 11 wherein the small negatively charged organic molecules are selected from the group consisting of primers, degraded dye molecules, deoxynucleotide triphosphates, and mixtures thereof.

13. The method of claim 12 wherein contacting the biological sample mixture with the surface comprising an anion exchange material partially coated with a negatively charged polymer is carried out under conditions effective to remove substantially all the primers from the biological sample mixture.

14. The method of claim 2 wherein the small negatively charged organic molecules have a molecular weight of less than about 6,000.

15. The method of claim 2 wherein contacting the biological sample mixture with the surface comprising an anion exchange material partially coated with a negatively charged polymer comprises agitating while contacting.

16. The method of claim 2 wherein the device is a microfluidic device.

17. A method of removing small negatively charged organic molecules from a biological sample mixture, the method comprising:
providing a device comprising a plurality of process arrays, wherein each process array of the plurality of process arrays comprises:
a plurality of process chambers, each of the process chambers defining a volume for containing a biological sample mixture; and
at least one distribution channel connecting the plurality of process chambers of the array; wherein at least one of the process arrays comprises a surface comprising quaternary ammonium ions partially coated with a negatively charged polyelectrolyte;
providing a biological sample mixture; and
contacting the biological sample mixture with the surface comprising quaternary ammonium ions partially coated with a negatively charged polyelectrolyte to remove at least a portion of the small negatively charged organic molecules from the biological sample mixture.

18. A method of removing small negatively charged organic molecules from a biological sample mixture, the method comprising:
providing a device comprising a plurality of process arrays, wherein each process array of the plurality of process arrays comprises:
a plurality of process chambers, each of the process chambers defining a volume for containing a biological sample mixture; and
at least one distribution channel connecting the plurality of process chambers of the array; wherein at least one of the process arrays comprises a surface comprising quaternary ammonium ions partially coated with a negatively charged polyelectrolyte;
providing a biological sample mixture; and
contacting the biological sample mixture with the surface comprising quaternary ammonium ions partially coated with a negatively charged polyelectrolyte to remove at least a portion of the small negatively charged organic molecules from the biological sample mixture;
wherein the biological sample mixture comprises a nucleic acid amplification reaction mixture.

19. The method of claim 18 wherein the device is a microfluidic device.

20. A method of removing small negatively charged organic molecules from a biological sample mixture, the method comprising:
providing a device comprising a plurality of process arrays, wherein each process array of the plurality of process arrays comprises:
a plurality of process chambers, each of the process chambers defining a volume for containing a biological sample mixture; and
at least one distribution channel connecting the plurality of process chambers of the array; wherein at least one of the process arrays comprises a surface comprising an anion exchange material partially coated with a negative polymer;
providing a biological sample mixture in the at least one process array, wherein the biological sample mixture comprises small negatively charged organic molecules having a molecular weight of less than about 6,000; and
transferring the biological sample mixture within the at least one process array, wherein the biological sample mixture and the surface comprising an anion exchange material remain in contact for a sufficient time to remove at least a portion of the small negatively charged organic molecules from the biological sample mixture.

21. A method of removing small negatively charged organic molecules from a biological sample mixture, the method comprising:
providing a device comprising a plurality of process arrays, wherein each process array of the plurality of process arrays comprises:
a plurality of process chambers, each of the process chambers defining a volume for containing a biological sample mixture; and
at least one distribution channel connecting the plurality of process chambers of the array; wherein at least one of the process arrays comprises a surface comprising an anion exchange material partially coated with a negatively charged polymer;
providing a biological sample mixture in the at least one process array; and
transferring the biological sample mixture within the at least one process array, wherein the biological sample mixture and the surface comprising an anion exchange material partially coated with a negatively charged polymer remain in contact for a sufficient time to remove at least a portion of the small negatively charged organic molecules from the biological sample mixture.

22. The method of claim 21 wherein the negatively charged polymer is a polyelectrolyte.

23. The method of claim 22 wherein the negatively charged polyelectrolyte is selected from the group consisting of a polystryene sulfonic acid, polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, salts thereof, and mixtures thereof.

24. The method of claim 21 wherein the anion exchange material comprises quaternary ammonium ions.

25. The method of claim 21 wherein the biological sample mixture is a nucleic acid sequencing reaction mixture.

26. The method of claim 25 wherein the small negatively charged organic molecules are selected from the group consisting of dye-labeled terminators, primers, degraded dye molecules, deoxynucleotide triphosphates, and mixtures thereof.

27. The method of claim 26 wherein the small negatively charged organic molecules comprise dye-labeled terminators.

28. The method of claim 27 wherein the dye-labeled terminators are selected from the group consisting of dideoxynucleotide triphosphates, dideoxynucleotide diphosphates, dideoxynucleotide monophosphates, dideoxynucleosides, and combinations thereof.

29. The method of claim 27 wherein the biological sample mixture and the surface comprising an anion exchange material partially coated with a negatively charged polymer are contacted under conditions effective to remove substantially all the dye-labeled terminators from the biological sample mixture.

30. The method of claim 21 wherein the biological sample mixture is a PCR reaction mixture.

31. The method of claim 30 wherein the small negatively charged organic molecules are selected from the group consisting of primers, degraded dye molecules, deoxynucleotide triphosphates, and mixtures thereof.

32. The method of claim 31 wherein the biological sample mixture and the surface comprising an anion exchange material partially coated with a negatively charged polymer are contacted under conditions effective to remove substantially all the primers from the biological sample mixture.

33. The method of claim 21 wherein the small negatively charged organic molecules have a molecular weight of less than about 6,000.

34. The method of claim 21 wherein the biological sample mixture and the surface comprising an anion exchange material partially coated with a negatively charged polymer are agitated while in contact.

35. The method of claim 21 wherein the at least one process array comprises a loading chamber and at least one process chamber.

36. A method of removing small negatively charged organic molecules from a biological sample mixture, the method comprising:
providing a device comprising a plurality of process arrays, wherein each process array of the plurality of process arrays comprises:
a plurality of process chambers, each of the process chambers defining a volume for containing a biological sample mixture; and
at least one distribution channel connecting the plurality of process chambers of the array; wherein at least one of the process arrays comprises a surface comprising quaternary ammonium ions partially coaxed with a negatively charged polyelectrolyte;
providing a biological sample mixture in the at least one process array; and
transferring the biological sample mixture within the at least one process array, wherein the biological sample mixture and the surface comprising quaternary ammonium ions partially coated with a negatively charged polyelectrolyte remain in contact for a sufficient time to remove at least a portion of the small negatively charged organic molecules from the biological sample mixture.

37. The mcthod of claim 36 wherein the biological sample mixture comprises a nucleic acid amplification reaction mixture.

38. The method of claim 36 wherein the biological sample mixture and the surface comprising quaternary ammoniom ions partially coated with a negatively charged polyelectrolyte are agitated while in contact.

39. A device comprising:
a plurality of process arrays, wherein each process array of the plurality of process arrays comprises:
a plurality of process chambers, each of the process chambers defining a volume for containing a biological sample mixture; and
at least one distribution channel connecting the plurality of process chambers of the array;
wherein at least one of the process arrays comprises a surface comprising an anion exchange material partially coated with a negatively charged polymer; and
wherein the device is operable to remove small negatively charged organic molecules from the biological sample mixture.

40. The device of claim 39 further comprising a plurality of valves, wherein at least one of the valves is located along the at least one distribution channel.

41. The device of claim 39 wherein the plurality of process arrays comprises a plurality of independent process arrays.

42. The device of claim 39 wherein the plurality of process arrays are arranged radially on the device.

43. The device of claim 39 wherein the negatively charged polymer is a polyelectrolyte.

44. The device of claim 39 wherein the anion exchange material, the negatively charged polymer, or both are pattern coated.

45. The device of claim 43 wherein the negatively charged polyelectrolyte is selected from the group consisting of a polystryene sulfonic acid, polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, salts thereof, and mixtures thereof.

46. The device of claim 39 wherein the anion exchange material comprises quaternized nitrogen.

47. A device comprising:
a plurality of process arrays, wherein each process array of the plurality of process arrays comprises:
a plurality of process chambers, each of the process chambers defining a volume for containing a biological sample mixture; and
at least one distribution channel connecting the plurality of process chambers of the array;
wherein at least one of the process arrays comprises a surface comprising quaternary ammonium ions partially coated with a negatively charged polyelectrolyte; and
wherein the device is operable to remove small negatively charged organic molecules from the biological sample mixture.

* * * * *

UNITED STATES PATENT AND TRADEMARK OFFICE
CERTIFICATE OF CORRECTION

PATENT NO. : 7,192,560 B2
APPLICATION NO. : 10/027222
DATED : March 20, 2007
INVENTOR(S) : Ranjani V. Parthasarathy It is certified that error appears in the above-identified patent and that said Letters Patent is hereby corrected as shown below:

Title Page
Item [56], References Cited, OTHER PUBLICATIONS, Delete "catologue" and insert -- catalogue --, therefor.
Item [56], References Cited, OTHER PUBLICATIONS, After "Internet:" delete "21".
Item [56], References Cited, OTHER PUBLICATIONS, Before "URL" insert -- < --.
Item [56], References Cited, OTHER PUBLICATIONS, Delete "22," and insert -- 22; --, therefor.

Column 2
Line 53, Delete "09/894,8 10" and insert -- 09/894,810 --, therefor.

Column 15
Line 12, Delete "entided" and insert -- entitled --, therefor.
Line 15, Delete "al.))." and insert -- al.)), --, therefor.
Line 30, Delete "METhODS;" and insert -- METHODS; --, therefor.

Column 17
Line 18, After "substrate" insert -- , --.
Line 18, After "layer" insert -- , --.

Column 21
Line 8, Delete "0.11" and insert -- 0.1 --, therefor.

Column 30
Line 27, In Claim 1, delete "mnaterial" and insert -- material --, therefor.

UNITED STATES PATENT AND TRADEMARK OFFICE
CERTIFICATE OF CORRECTION

PATENT NO. : 7,192,560 B2
APPLICATION NO. : 10/027222
DATED : March 20, 2007
INVENTOR(S) : Ranjani V. Parthasarathy It is certified that error appears in the above-identified patent and that said Letters Patent is hereby corrected as shown below:

Column 32
Line 27, In Claim 20, delete "negative" and insert -- negatively charged --, therefor.

Column 33
Line 61, In Claim 36, delete "coaxed" and insert -- coated --, therefor.

Column 34
Line 7, In Claim 37, delete "mcthod" and insert -- method --, therefor.
Line 11, In Claim 38, delete "ammoniom" and insert -- ammonium --, therefor.

Signed and Sealed this

Fourth Day of November, 2008

JON W. DUDAS
*Director of the United States Patent and Trademark Office*